(12) United States Patent
Hecker et al.

(10) Patent No.: US 9,120,796 B2
(45) Date of Patent: Sep. 1, 2015

(54) B-LACTAMASE INHIBITOR PICOLINE SALT

(71) Applicant: Cubist Pharmaceuticals, Inc., Lexington, MA (US)

(72) Inventors: Evan A. Hecker, Arlington, MA (US); Amy Baldwin, Waltham, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/504,860

(22) Filed: Oct. 2, 2014

(65) Prior Publication Data

US 2015/0094472 A1    Apr. 2, 2015

Related U.S. Application Data

(60) Provisional application No. 61/885,683, filed on Oct. 2, 2013.

(51) Int. Cl.
C07D 471/08         (2006.01)

(52) U.S. Cl.
CPC .................................. *C07D 471/08* (2013.01)

(58) Field of Classification Search
CPC ............................................. C07D 471/08
USPC .......................................... 546/121; 514/300
See application file for complete search history.

(56) References Cited

U.S. PATENT DOCUMENTS

| | | | |
|---|---|---|---|
| 2,789,132 A | 4/1957 | Surean | |
| 4,684,722 A | 8/1987 | Sundeen | |
| 4,826,973 A | 5/1989 | Anderson et al. | |
| 5,173,485 A | 12/1992 | Sakane et al. | |
| 5,194,604 A | 3/1993 | Denzel et al. | |
| 6,034,107 A | 3/2000 | Hirai et al. | |
| 6,194,442 B1 | 2/2001 | Hirai et al. | |
| 6,416,979 B1 | 7/2002 | Hirai et al. | |
| 6,953,807 B2 | 10/2005 | Hutin et al. | |
| 7,112,592 B2 | 9/2006 | Lampilas et al. | |
| 7,129,232 B2 | 10/2006 | Ohki et al. | |
| 7,612,087 B2 | 11/2009 | Aszodi et al. | |
| 7,732,610 B2 | 6/2010 | Lampilas et al. | |
| 7,786,044 B2 | 8/2010 | Yerkes et al. | |
| 8,003,799 B2 | 8/2011 | Nieto-Roman et al. | |
| 8,178,554 B2 | 5/2012 | Lampilas et al. | |
| 8,268,753 B2 | 9/2012 | Epps et al. | |
| 8,288,553 B2 | 10/2012 | Priour et al. | |
| 8,471,025 B2 | 6/2013 | Dedhiya et al. | |
| 8,487,093 B2 | 7/2013 | Blizzard et al. | |
| 2009/0227554 A1 | 9/2009 | Liversidge | |
| 2010/0197928 A1 | 8/2010 | Priour et al. | |
| 2010/0286031 A1 | 11/2010 | Charan et al. | |
| 2011/0046102 A1 | 2/2011 | Ledoussal et al. | |
| 2011/0257079 A1 | 10/2011 | Chaudhary | |
| 2011/0294777 A1 | 12/2011 | Blizzard et al. | |
| 2012/0053350 A1 | 3/2012 | Mangion et al. | |
| 2012/0165533 A1 | 6/2012 | Abe et al. | |
| 2012/0323010 A1 | 12/2012 | Ronsheim et al. | |
| 2013/0012712 A1 | 1/2013 | Priour et al. | |
| 2013/0059774 A1 | 3/2013 | Patel et al. | |
| 2013/0225554 A1 | 8/2013 | Maiti et al. | |
| 2013/0267480 A1 | 10/2013 | Dedhiya et al. | |
| 2013/0289012 A1 | 10/2013 | Gu et al. | |
| 2013/0296290 A1 | 11/2013 | Gu et al. | |
| 2013/0296291 A1 | 11/2013 | Gu et al. | |
| 2013/0296292 A1 | 11/2013 | Gu et al. | |
| 2013/0296293 A1 | 11/2013 | Gu et al. | |
| 2013/0296555 A1 | 11/2013 | Gu et al. | |
| 2013/0303504 A1 | 11/2013 | Gu et al. | |
| 2013/0345190 A1 | 12/2013 | Gu et al. | |
| 2014/0275001 A1 | 9/2014 | Gu et al. | |

FOREIGN PATENT DOCUMENTS

| | | |
|---|---|---|
| EP | 0229012 A1 | 7/1989 |
| EP | 2135959 A1 | 12/2009 |
| FR | 2812635 A | 2/2002 |
| FR | 2835186 A | 8/2003 |
| FR | 2930553 A1 | 10/2009 |
| FR | 2951171 A | 4/2011 |
| KR | 2010130176 A | 12/2010 |
| WO | 02010172 A1 | 7/2002 |
| WO | 03063864 A2 | 8/2003 |
| WO | 2005108391 A1 | 11/2005 |
| WO | 2006125974 A1 | 11/2006 |
| WO | 2007129176 A2 | 11/2007 |
| WO | 2009091856 A2 | 7/2009 |
| WO | 2009133442 A1 | 11/2009 |
| WO | 2010056827 A1 | 5/2010 |
| WO | 2010118361 A1 | 10/2010 |
| WO | 2010126820 A1 | 11/2010 |
| WO | 2011042560 A1 | 4/2011 |
| WO | 2011101710 A1 | 8/2011 |

(Continued)

OTHER PUBLICATIONS

Crompton, et al: Beta-Lactamase inhibitors, the inhibition of serine beta-lactamases by specific boronic acids; Biochem J., 1988, vol. 251, pp. 453-459.

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture—activity relationships in the S-3578 series"; Bioorganic and Medicinal Chemistry 2004, vol. 12, pp. 4211-4219.

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-yl)-2-ethoxyiminoacetamido] cephalosporins bearing 4-[3-(aminoalkyl)-ureido]-1-pyridinium at C-3'"'; Bioorganic and Medicinal Chemistry 2004, vol. 12, pp. 4221-4231.

(Continued)

*Primary Examiner* — Niloofar Rahmani
(74) *Attorney, Agent, or Firm* — Lathrop & Gage LLP; Brian C. Trinque

(57) ABSTRACT

Provided herein are intermediates useful in the synthesis of β-lactamase inhibitors, and methods of making said intermediates and β-lactamase inhibitors.

22 Claims, 26 Drawing Sheets

(56) References Cited

FOREIGN PATENT DOCUMENTS

| WO | 2012086241 | A1 |   | 6/2012 |
|----|------------|----|---|--------|
| WO | 2012172368 | A1 |   | 12/2012 |
| WO | 2013014496 | A1 |   | 1/2013 |
| WO | 2013014497 | A1 |   | 1/2013 |
| WO | 2013030735 |    | * | 3/2013 |
| WO | 2013030735 | A1 |   | 3/2013 |
| WO | 2013038330 | A1 |   | 3/2013 |
| WO | 2013149121 | A1 |   | 10/2013 |
| WO | 2013180197 | A1 |   | 12/2013 |

OTHER PUBLICATIONS

Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure-activity Relationships"; The Journal of Antibiotics 2002, vol. 55, No. 11, pp. 975-992.

Blizzard et al, Side chain SAR of bicyclic beta-lacftamase inhibitors (BLIs). 1. discovery of a class C BLI for combination with imipinem; Bioorganic & Medicinal Chemistry Letters; 2010, vol. 20, pp. 918-921.

Coleman, Diazabicyclooctanes (DBOs) a potent new class of non-beta-lactam beta-lactamase inhibitors; Current Opinion in Micorbiology; 2011, vol. 14, pp. 1-6.

Miller et al, Practical and Cost-Effective Manufacturing Route for the Synthesis of a beta-lactamase Inhibitor; Organic Letters, 2014, vol. 16, No. 1, pp. 174-177.

International Search Report, PCT/US2014/058797, dated Nov. 28, 2014, 2 pages.

Manchand et al. 'A Novel Synthesis of the Monobactam Antibiotic Carumonam.' Journal of Organic Chemistry. 1988, vol. 53, pp. 5507-5512.

Mangion et al. 'A concise synthesis of a β-lactamase inhibitor.' Organic Letters. 2011, vol. 13, No. 20, pp. 5480-5483.

Anderson, Neal G. 'Case Studies on the Development of Two Drugs, the 1980's and Today.' Presented to the University of Wisconsin. Oct. 5, 2011. (7 pages).

Fieser et al. "Reagents for Organic Synthesis, 2Wiley-Interscience." New York (1967): 1127-1128.

Gilbert, Everett E. 'The Reactions of Sulfur Trioxide, and of it's Adducts, with Organic Compounds.' Allied Chemical Corporation, General Chemical Division. Nov. 1961. pp. 549-589.

Hertzberg et al. 'Carotenoid sulfates. 4. syntheses and properties of carotenoid sulfates.' Acta Chemica Scandinavica B. 1985, vol. 39, pp. 629-638.

Ramdahl et al. 'Carotenoid sulfates. 1. Partial syntheses of lycoxanthin sulfate and zeaxanthin disulfate.' ACTA Chemica Scandinavica Series B-Organic Chemistry and Biochemistry. 1980, vol. 34, No. 10, pp. 773-774.

U.S. Appl. No. 14/206,127, filed Mar. 12, 2014, 244 pages.

* cited by examiner

| Angle 2θ (±0.2) | Relative Intensity |
|---|---|
| 10.48 | 57% |
| 11.69 | |
| 12.00 | |
| 12.81 | |
| 14.28 | |
| 15.19 | |
| 15.69 | |
| 16.19 | |
| 16.75 | 100% |
| 17.50 | |
| 17.70 | |
| 18.27 | 22% |
| 19.58 | |
| 20.40 | 20% |
| 20.79 | |
| 21.24 | |
| 21.85 | |
| 22.48 | |
| 23.55 | |
| 24.02 | |
| 24.26 | |

| Angle 2θ (±0.2) | Relative Intensity |
|---|---|
| 25.39 | |
| 25.66 | |
| 26.69 | |
| 26.82 | |
| 27.33 | |
| 28.19 | |
| 28.80 | 17% |
| 29.16 | |
| 29.38 | |
| 29.82 | |
| 30.46 | |
| 31.21 | |
| 31.67 | |
| 32.19 | |
| 32.63 | |
| 33.40 | |
| 33.89 | |
| 34.25 | |
| 35.39 | |
| 35.73 | |
| 35.96 | |
| 36.30 | |
| 37.82 | |
| 38.72 | |
| 38.83 | |

*Fig. 1B*

| Method | Column | MPA | MPB | Gradient | | | Detection |
|---|---|---|---|---|---|---|---|
| HPLC 1 | Waters XSelect CSH C18 | 30 mM Na phosphate, pH 2.5 | ACN | Time (min) | %MPA | %MPB | 215nm |
| | | | | 0.0 | 100 | 0 | |
| | | | | 3.0 | 100 | 0 | |
| | | | | 18.0 | 67 | 33 | |
| | | | | 23.0 | 67 | 33 | |
| | | | | 23.1 | 100 | 0 | |
| | | | | 30.0 | 100 | 0 | |
| HPLC 2 | Waters Xbridge BEH Shield RP18 | 0.01% TFA in water | 0.01% TFA in ACN | Time (min) | %MPA | %MPB | 215nm |
| | | | | 0.00 | 100 | 0 | |
| | | | | 1.00 | 80 | 20 | |
| | | | | 12.00 | 20 | 80 | |
| | | | | 12.01 | 10 | 90 | |
| | | | | 14.00 | 10 | 90 | |
| | | | | 14.01 | 100 | 0 | |
| | | | | 20.00 | 100 | 0 | |
| HPLC 3 | Waters Sunfire C18 | Water + 0.01% TFA | Acetonitrile + 0.01% TFA | Time (min) | %A | %B | 215nm |
| | | | | 0.00 | 100 | 0 | |
| | | | | 2.00 | 100 | 0 | |
| | | | | 5.00 | 70 | 30 | |
| | | | | 8.00 | 10 | 90 | |
| | | | | 8.01 | 100 | 0 | |
| | | | | 10.00 | 100 | 0 | |
| HPLC 4 | Waters XSelect HSS T3, 150 x 4.6mm x 2.5um | Water + 0.01% TFA | Acetonitrile + 0.01% TFA | Time (min) | %A | %B | 230nm |
| | | | | 0.00 | 100 | 0 | |
| | | | | 4.00 | 92 | 8 | |
| | | | | 10 | 5 | 95 | |
| | | | | 10.1 | 100 | 0 | |
| | | | | 15 | 100 | 0 | |

*Fig. 18*

| Time (days) | 4 °C in Water | | | RT in Water | | | 4 °C in DCM | | | RT in DCM | | |
|---|---|---|---|---|---|---|---|---|---|---|---|---|
| | % Purity | % T0 Purity | Area | % Purity | % T0 Purity | Area | % Purity | % T0 Purity | Area | % Purity | % T0 Purity | Area |
| 0 | 97.5% | 100% | 1094074 | 97.9% | 100% | 1149142 | 97.8% | 100% | 1143847 | 97.7% | 100% | 1137769 |
| 0.2 | 97.5% | 100% | 1138790 | 97.6% | 100% | 1127413 | 97.7% | 100% | 1104092 | 97.3% | 100% | 1110128 |
| 1 | 97.3% | 100% | 1129771 | 97.4% | 99% | 1103797 | 97.4% | 100% | 1071894 | 97.5% | 100% | 1101331 |
| 2 | 97.5% | 100% | 1122658 | 97.4% | 99% | 1078421 | 97.5% | 100% | 1088309 | 97.5% | 100% | 1020960 |
| 3 | 97.5% | 100% | 1115381 | 97.3% | 99% | 1082352 | 97.4% | 100% | 1109936 | 97.4% | 100% | 1062992 |
| 7 | 97.1% | 100% | 1123755 | 96.4% | 98% | 1034852 | 97.0% | 99% | 1071826 | 97.4% | 100% | 1073391 |
| 14 | 96.9% | 99% | 1054123 | 92.8% | 95% | 927376 | | | 1090146 | 97.3% | 100% | 1073157 |
| % RSD | | | 2.59% | | | 6.86% | | | 2.29% | | | 3.48% |

*Fig. 21B*

| Time (hours) | RT in DCM | | |
|---|---|---|---|
| | % Purity | % T0 Purity | Area |
| 72 | 34.48% | 100.0% | 541063 |
| 96 | 36.93% | 107.1% | 873157 |
| 120 | 33.19% | 96.3% | 784274 |
| 144 | 31.47% | 91.3% | 754572 |
| 240 | 23.30% | 67.6% | 603640 |
| % RSD | | | 19.1% |

*Fig. 22B*

|  | T-0 | T-14Day -20 °C | T-14Day 4 °C | T-14Day 25 °C/60% RH |
|---|---|---|---|---|
| Purity (% AUC) | 99.6% | 99.5% | 99.5% | 99.3% |
| % of T-0 | -- | 99.9% | 99.9% | 99.7% |
| Potency (µg/mg) | 785µg/mg | 781µg/mg | 786µg/mg | 779µg/mg |
| % of T-0 | -- | 99.5% | 100% | 99.2% |

Fig. 23

β-LACTAMASE INHIBITOR PICOLINE SALT

RELATED APPLICATION

This application claims priority to U.S. Provisional Application No. 61/885,683, filed Oct. 2, 2013. The content of this application is incorporated herein by reference it its entirety.

TECHNICAL FIELD

This disclosure is directed to β-lactamase inhibitors (BLIs) and related methods of manufacture. Specifically, this disclosure provides a picoline salt of (2S,5R)-2-(1,3,4-oxadiazol-2-yl)-7-oxo-1,6-diazabicyclo[3.2.1]octan-6-yl hydrogen sulfate, a crystalline form of the picoline salt, and methods of making the picoline salt. Also provided herein are methods of making a sodium salt of (2S,5R)-2-(1,3,4-oxadiazol-2-yl)-7-oxo-1,6-diazabicyclo[3.2.1]octan-6-yl hydrogen sulfate from the picoline salt.

BACKGROUND

Bacterial resistance to β-lactam antibiotics, especially in Gram-negative bacteria, is most commonly mediated by β-lactamases. β-lactamases are enzymes that catalyze the hydrolysis of the β-lactam ring, which inactivates the antibacterial activity of the β-lactam antibiotic and allows the bacteria to become resistant. Inhibition of the β-lactamase with a BLI slows or prevents degradation of the β-lactam antibiotic and restores β-lactam antibiotic susceptibility to β-lactamase producing bacteria. Many of these β-lactamases are not effectively inhibited by BLIs currently on the market rendering the β-lactam antibiotics ineffective in treating bacteria that produce these β-lactamases. There is an urgent need for novel BLIs that inhibit β-lactamases that are not effectively inhibited by the current clinical BLIs (e.g., KPC, class C and class D β-lactamases) and that could be used in combination with β-lactam antibiotics to treat infections caused by β-lactam resistant bacteria.

In chemical synthesis (particularly large scale processes), column chromatography can be expensive and problematic. For example, column materials and solvents are costly, chromatographic separation can be inefficient and time-consuming, and compound degradation on the column can result in lower product yields. In contrast, precipitation or crystallization methods are preferred as they are less expensive and more process-friendly, avoiding many of the problems described above.

The compound of Formula (III) (referred to herein as "Formula (III)") is a β-lactamase inhibitor that is described in U.S. application Ser. No. 13/853,327 (U.S. Publication No. US 2013/0296290). Formula (III) can be prepared by methods wherein intermediates are purified by column chromatography. Thus, there is a need to develop methods for preparing the BLIs (e.g., a compound of Formula (III)) which comprise isolating or purifying intermediates by precipitation or crystallization.

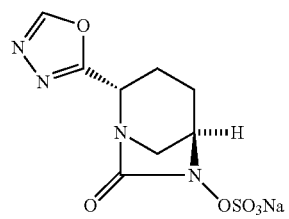

Formula (III)

SUMMARY

Provided herein is a compound of Formula (II):

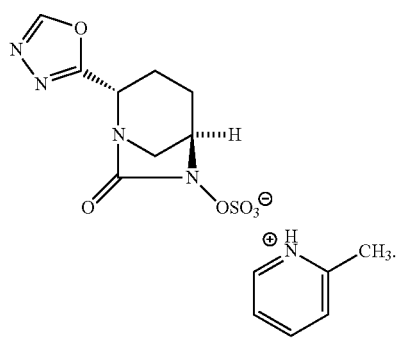

Formula (II)

In one embodiment, the compound of Formula (II) is crystalline. Thus, in one embodiment, the crystalline compound of Formula (II) is characterized by an X-ray powder diffraction pattern substantially in accordance with FIG. 1A. In another embodiment, the crystalline compound of Formula (II) is characterized by a differential scanning calorimetry thermogram substantially in accordance with FIG. 2, FIG. 7, or FIG. 12. In another embodiment, the crystalline compound of Formula (II) is characterized by a thermogravimetry curve substantially in accordance with FIG. 3, FIG. 8, and FIG. 13.

In another aspect, provided herein is a method of making the compound of Formula (II), the method comprising the step of reacting a compound of Formula (I):

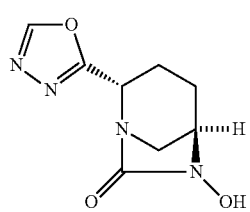

Formula (I)

with a 2-picoline/sulfur trioxide complex in a solvent to form the compound of Formula (II).

In another aspect, provided herein is a method for preparing the compound of Formula (III) from the compound of Formula (II):

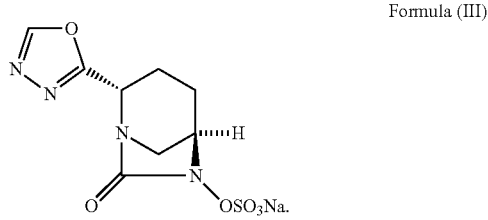

Formula (III)

In one embodiment of the method, the compound of Formula (III) is a trihydrate. In one embodiment, the method comprises the step of reacting the compound of Formula (II) with a sodium salt, in a solvent, to form the compound of Formula (III). In one embodiment of this method, the solvent comprises water. In another embodiment, the sodium salt is sodium bicarbonate.

In another embodiment, the method comprises the steps of: a) reacting a compound of Formula (I) with a 2-picoline/sulfur trioxide complex in a solvent to form the compound of Formula (II); b) crystalizing the compound of Formula (II); and c) reacting the compound of Formula (II) with a sodium salt in a solvent to form the compound of Formula (III).

In one embodiment of this method, the solvent of step a) comprises dichloromethane. In another embodiment, the solvent of step c) comprises water. In still another embodiment, the sodium salt is sodium bicarbonate. In a particular embodiment, the solvent of step a) comprises dichloromethane, the solvent of step c) comprises water, and the sodium salt is sodium bicarbonate.

In another embodiment, the solvent of step c) comprises isopropyl acetate. In a further embodiment, the solvent of step c) comprises isopropyl acetate and water. In still another embodiment, the sodium salt is sodium 2-ethylhexanoate. In a particular embodiment, the solvent of step a) comprises dichloromethane, the solvent of step c) comprises isopropyl acetate and water, and the sodium salt is sodium 2-ethylhexanoate.

BRIEF DESCRIPTION OF THE FIGURES

FIG. 1B is a table showing the 2θ values of peaks present in the X-ray diffraction patterns of a crystalline form of Formula (II).

FIG. 18 is a summary of the HPLC methods used in composition analysis.

FIG. 21B is a table showing the data used to generate FIG. 21A.

FIG. 22B is a table showing the data used to generate FIG. 22A.

FIG. 23 is a table showing the stability of the picoline salt of (2S,5R)-2-(1,3,4-oxadiazol-2-yl)-7-oxo-1,6-diazabicyclo[3.2.1]octan-6-yl hydrogen sulfate isolated solid at 2 weeks (see Example 10).

DETAILED DESCRIPTION

Figure 1A:
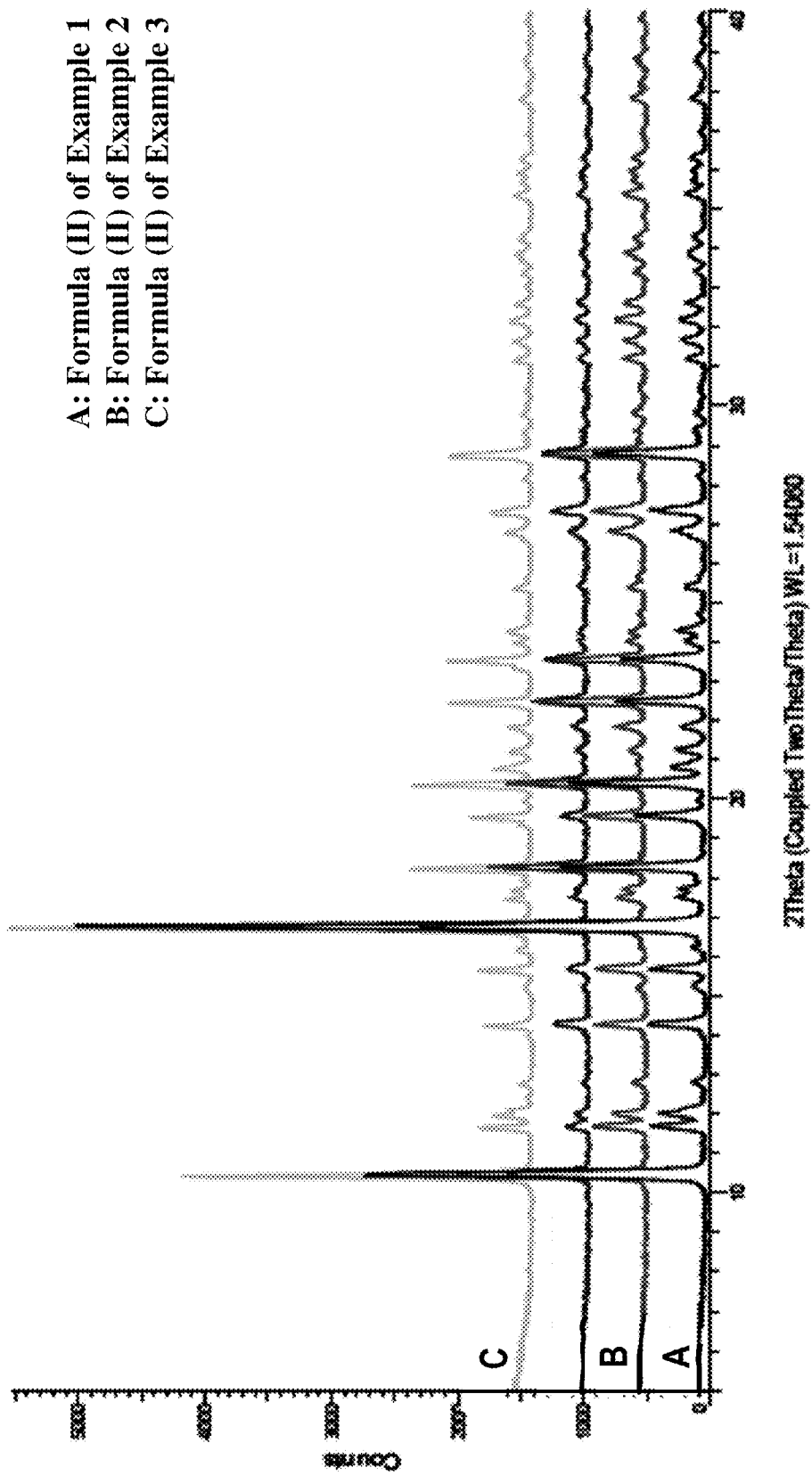
FIG. 1A depicts the X-ray powder diffraction pattern of Formula (II) of Example 1, Formula (II) of Example 2, and Formula (II) of Example 3.

Provided herein are picoline salts of (2S,5R)-2-(1,3,4-oxadiazol-2-yl)-7-oxo-1,6-diazabicyclo[3.2.1]octan-6-yl hydrogen sulfate, i.e., 2-methylpyridin-1-ium (2S,5R)-2-(1,3,4-oxadiazol-2-yl)-7-oxo-1,6-diazabicyclo[3.2.1]octan-6-yl sulfate, 3-methylpyridin-1-ium (2S,5R)-2-(1,3,4-oxadiazol-2-yl)-7-oxo-1,6-diazabicyclo[3.2.1]octan-6-yl sulfate, and 4-methylpyridin-1-ium (2S,5R)-2-(1,3,4-oxadiazol-2-yl)-7-oxo-1,6-diazabicyclo[3.2.1]octan-6-yl sulfate. These picoline salts can comprise 2-picoline (Formula (II)), 3-picoline (Formula (IIa)), or 4-picoline (Formula (IIb)), having the structures:

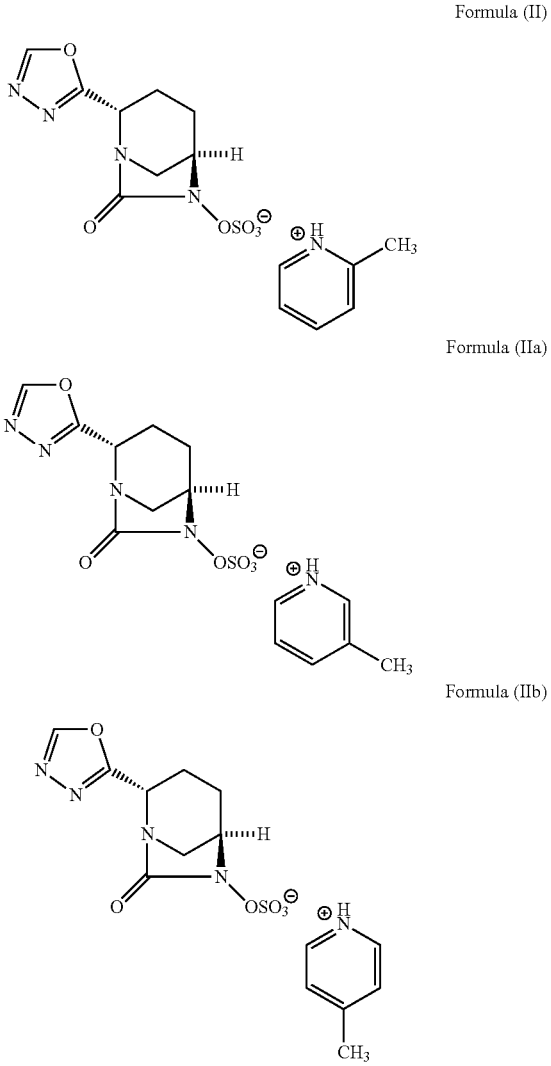

Formula (II)

Formula (IIa)

Formula (IIb)

The compound of Formula (II) is the 2-picoline salt of (2S,5R)-2-(1,3,4-oxadiazol-2-yl)-7-oxo-1,6-diazabicyclo[3.2.1]octan-6-yl hydrogen sulfate, i.e., 2-methylpyridin-1-ium (2S,5R)-2-(1,3,4-oxadiazol-2-yl)-7-oxo-1,6-diazabicyclo[3.2.1]octan-6-yl sulfate. A particular form of the compound of Formula (II) exhibits unexpectedly high crystallinity and favorable solubility characteristics (e.g., low solubility), which are properties that are useful in chemical synthesis procedures for the purpose of avoiding (or reducing the number of) chromatographic separations (e.g., purification) or chromatographic transformations (e.g., ion exchange).

Provided herein is a compound of Formula (II). In some embodiments, the compound of Formula (II) is crystalline. Also provided are methods of making a compound of Formula (II), particularly crystalline Formula (II). These methods are advantageous in a number of respects.

For example, upon formation by a reaction between the compound of Formula (I) and 2-picoline/sulfur trioxide complex, the compound of Formula (II) can be isolated from the reaction mixture by crystallization (see, e.g., Examples 1 and 2). Accordingly, in one aspect, provided herein is a method of making a compound of Formula (II), the method comprising the step of reacting a compound of Formula (I):

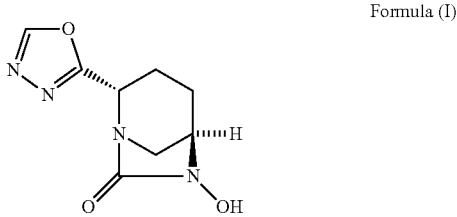 [SMILES: O=C1N(O)[C@@H]2CC[C@@H](c3nnco3)N1C2]

Formula (I)

with a 2-picoline/sulfur trioxide complex in a solvent to form the compound of Formula (II). In one embodiment, the method further comprises the step of combining chlorosulfonic acid and 2-picoline to form the 2-picoline/sulfur trioxide complex. In another embodiment, the solvent comprises dichloromethane. The synthesis of a compound of Formula (I) is described in Example 11 and in U.S. Publication No. US 2013/0296290, which is hereby incorporated by reference in its entirety.

In another aspect, provided herein is a method of making the compound of Formula (II), the method comprising the step of combining a compound of Formula (I) with 2-picoline and chlorosulfonic acid, such that the compound of Formula (II) is formed.

In some embodiments, the methods further comprise isolating the compound of Formula (II). In a particular embodiment, the method further comprises crystallizing the compound of Formula (II). The step of crystallizing the compound of Formula (II) can be carried out without addition of any anti-solvents (see, e.g., Examples 1 and 3), or with addition of THF as an anti-solvent (see, e.g., Examples 2 and 4).

It has also been demonstrated that these synthesis methods, including the crystallization process, can be scaled up (see, e.g., Examples 3 and 4). For example, a crystalline form of the compound of Formula (II) was obtained at similar yields when these methods were carried out without addition of any anti-solvents at 1 gram scale (see Example 1, Yield: 63%) and at 7.35 gram scale (see Example 3, Yield: 70.5%). A crystalline form of the compound of Formula (II) was also obtained at similar yields when these methods were carried out with addition of THF as an anti-solvent at 1 gram scale (see Example 2, Yield: 96%) and 10 gram scale (see Example 4, Yield: 88%). Thus, these methods are useful, at least, for large scale manufacturing of an intermediate in the synthesis of the β-lactamase inhibitor of Formula (III).

Isolation of the compound of Formula (II) by crystallization can also improve the purity and quality of the product. In certain embodiments, the compound of Formula (II) that was not isolated by crystallization was found to have a significantly lower purity and quality (see Example 5). Accordingly, in one particular embodiment, provided herein is a method for preparing the crystalline compound of Formula (II), the method comprising reacting a compound of Formula (I) with a 2-picoline/sulfur trioxide complex in a solvent, and crystallizing the compound of Formula (II) from the reaction mixture.

Surprisingly, it has been found that compounds that are structurally related to 2-picoline (i.e., tetrabutylammonium, pyridine, 5-ethyl-2-methylpyridine or 2,6-lutidine) cannot be combined with the compound of Formula (I) and chlorosulfonic acid to form crystalline salts that precipitate from the reaction mixture. Therefore, these close structural analogues of 2-picoline cannot be used to produce a high purity and quality product (see Examples 6, 7, and 10). Thus, the crystalline compound of Formula (II) is unexpectedly superior to analogous compounds for the manufacture of the compound of Formula (III).

Polymorphism

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, stability, solubility, dissolution rate, etc., which can, in turn, affect the stability, dissolution rate and/or bioavailability of a given polymorph and its suitability for use as a pharmaceutical and in pharmaceutical compositions.

Different polymorphs of a compound (e.g., the picoline salt having Formula (II)) can incorporate different impurities, or chemical residues, upon crystallization. Certain polymorphs incorporate very little, or no, chemical residues. Accordingly, the formation of certain polymorph forms of a compound may result in purification of the compound.

Characterization of Polymorphs

In certain embodiments, the compounds of the invention are identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials.

In one embodiment, the crystalline compound of Formula (II) is characterized by an X-ray powder diffraction pattern substantially in accordance with Spectrum A, Spectrum B or Spectrum C of FIG. 1A.

In another embodiment, the crystalline compound of Formula (II) is characterized by a X-ray powder diffraction pattern comprising one or more characteristic peaks expressed in degrees 2θ (±0.2) as listed in the table of FIG. 1B.

In an embodiment the crystalline compound of Formula (II) is characterized by a X-ray powder diffraction pattern comprising characteristic peaks expressed in degrees 2θ (±0.2) at 10.48, 16.75, 18.27, 20.40, and 28.80.

In another embodiment, the crystalline compound of Formula (II) is characterized by a X-ray powder diffraction pattern comprising characteristic peaks expressed in degrees 2θ (±0.2) at 10.48, 11.69, 12.00, 12.81, 14.28, 15.69, 16.75, 17.50, 17.70, 18.27, 19.58, 20.40, 21.24, 21.85, 22.48, 23.55, 24.02, 24.26, 25.39, 26.8, 27.33, 28.80, 31.21, 31.67, 32.19, 32.63, 33.89, 35.73, 35.96, 36.30, and 37.82.

In another embodiment, the crystalline compound of Formula (II) is characterized by a X-ray powder diffraction pattern comprising characteristic peaks expressed in degrees 2θ (±0.2) at 10.48, 11.69, 12.00, 12.81, 14.28, 15.19, 15.69, 16.19, 16.75, 17.50, 17.70, 18.27, 19.58, 20.40, 20.79, 21.24, 21.85, 22.48, 23.55, 24.02, 24.26, 25.39, 25.66, 26.69, 26.82, 27.33, 28.19, 28.80, 29.16, 29.38, 29.82, 30.46, 31.21, 31.67, 32.19, 32.63, 33.40, 33.89, 34.25, 35.39, 35.73, 35.96, 36.30, 37.82, 38.72, and 38.83.

The compounds of the invention may also be defined by their differential scanning calorimetry (DSC) thermograms. In a particular embodiment, the crystalline compound of Formula (II) is characterized by a differential scanning calorimetry thermogram having a characteristic endotherm peak at 139.94±10° C. In another particular embodiment, the crystalline compound of Formula (II) is characterized by a differential scanning calorimetry thermogram having a characteristic endotherm peak at about 139.94° C. In another particular embodiment, the crystalline compound of Formula (II) is characterized by a differential scanning calorimetry thermogram having a characteristic endotherm peak at about 139.84° C. In another particular embodiment, the crystalline compound of Formula (II) is characterized by a differential scanning calorimetry thermogram having a characteristic endotherm peak at about 139.18° C. In another particular embodiment, the crystalline compound of Formula (II) is characterized by a differential scanning calorimetry thermogram having a characteristic endotherm peak at about 130.45° C.

In another particular embodiment, the crystalline compound of Formula (II) is characterized by a differential scanning calorimetry thermogram having a characteristic endotherm peak at 60.31±10° C. In another particular embodiment, the crystalline compound of Formula (II) is characterized by a differential scanning calorimetry thermogram having a characteristic endotherm peak at about 60.31° C. In another particular embodiment, the crystalline compound of Formula (II) is characterized by a differential scanning calorimetry thermogram having a characteristic endotherm peak at about 68.92° C. In another particular embodiment, the crystalline compound of Formula (II) is characterized by a differential scanning calorimetry thermogram having a characteristic endotherm peak at about 55.62° C.

In still another embodiment, the crystalline compound of Formula (II) is characterized by a differential scanning calorimetry thermogram having an exotherm peak at 181.77±10° C. In one particular embodiment, the differential scanning calorimetry thermogram has an exotherm peak at about 181.77° C. In another particular embodiment, the differential scanning calorimetry thermogram has an exotherm peak at about 175.18° C.

Figure 2:
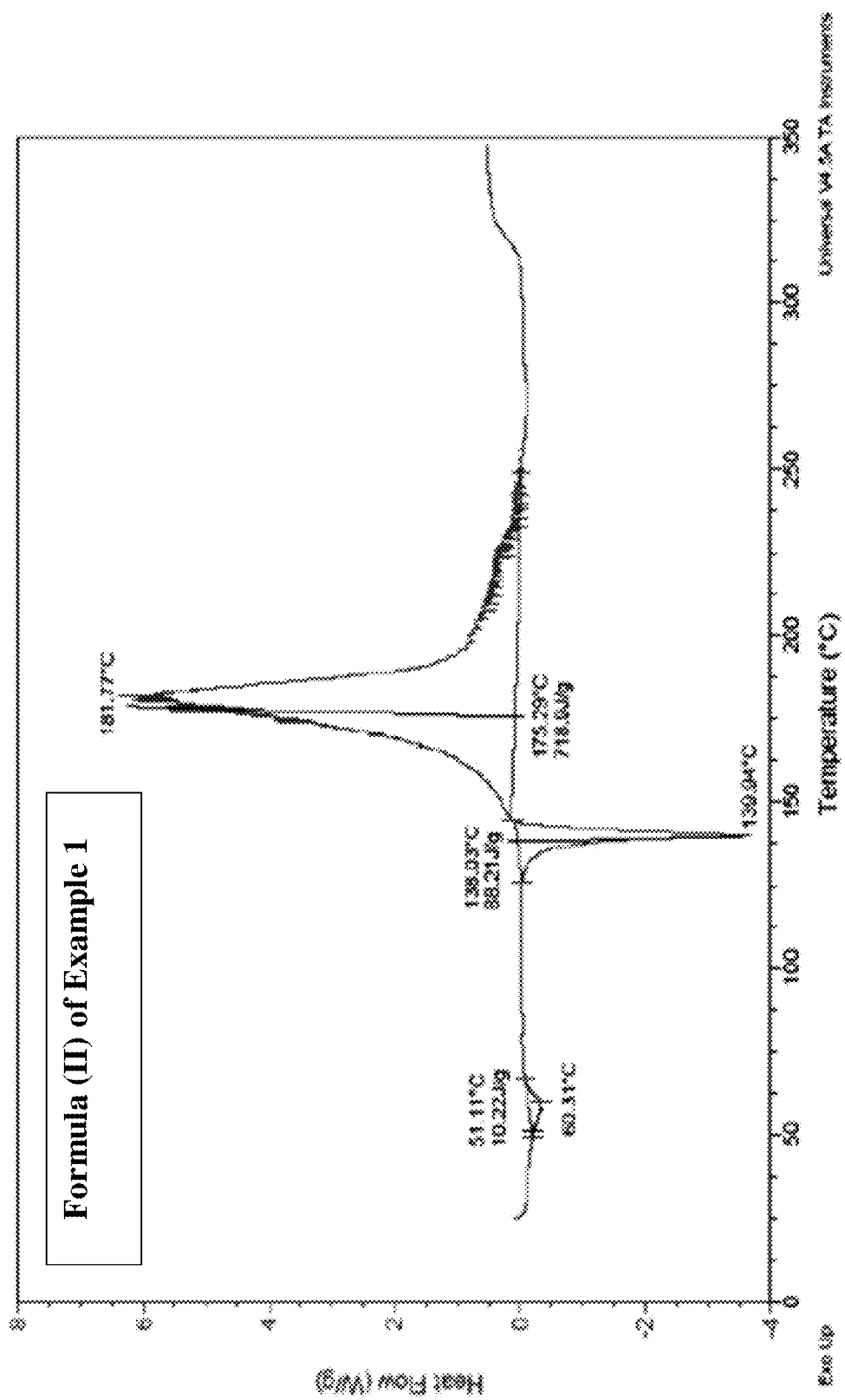
FIG. 2 depicts the differential scanning calorimetry (DSC) of Formula (II) of Example 1.
Figure 7:
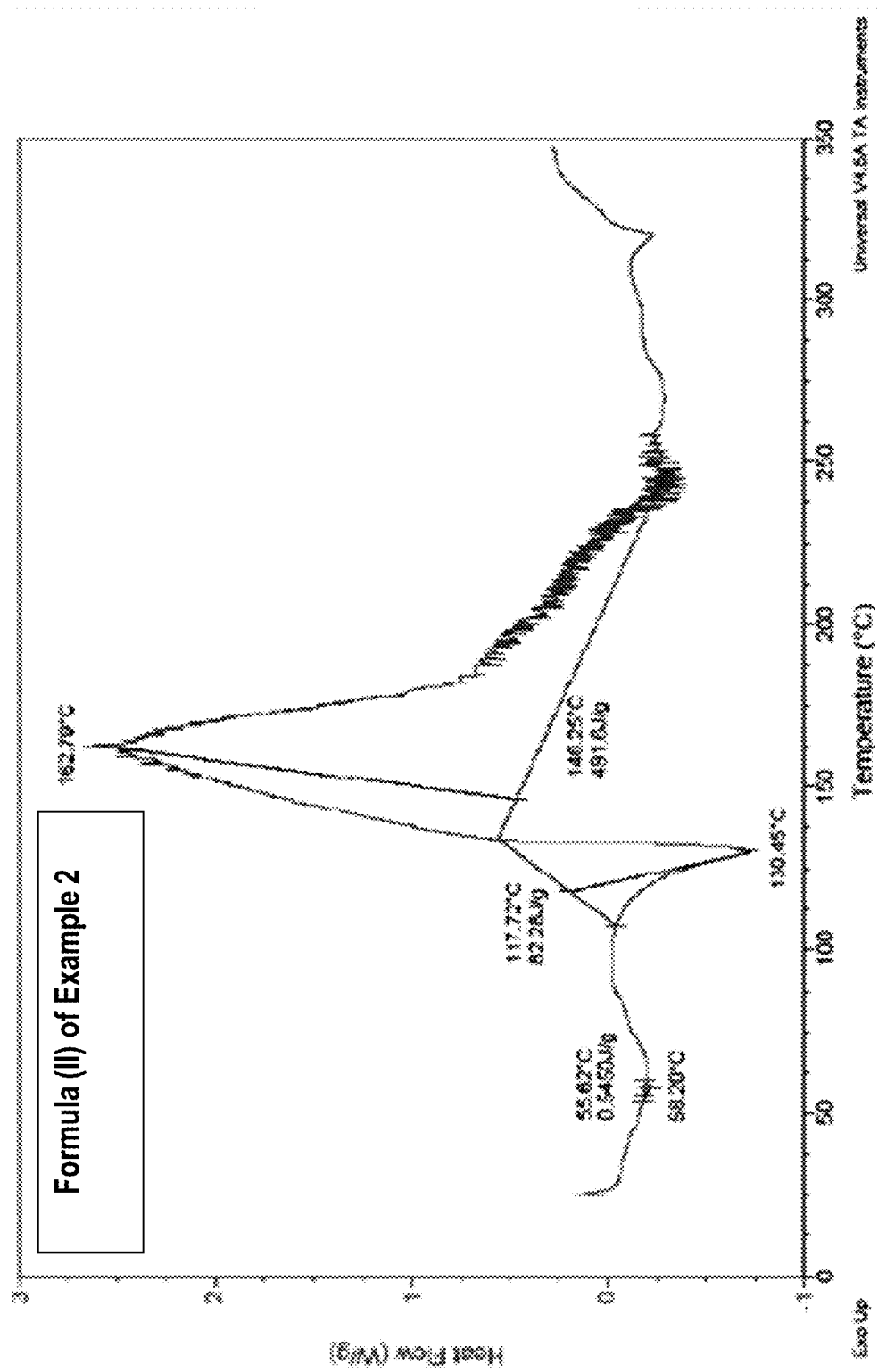
FIG. 7 depicts the differential scanning calorimetry (DSC) of Formula (II) of Example 2.
Figure 12:
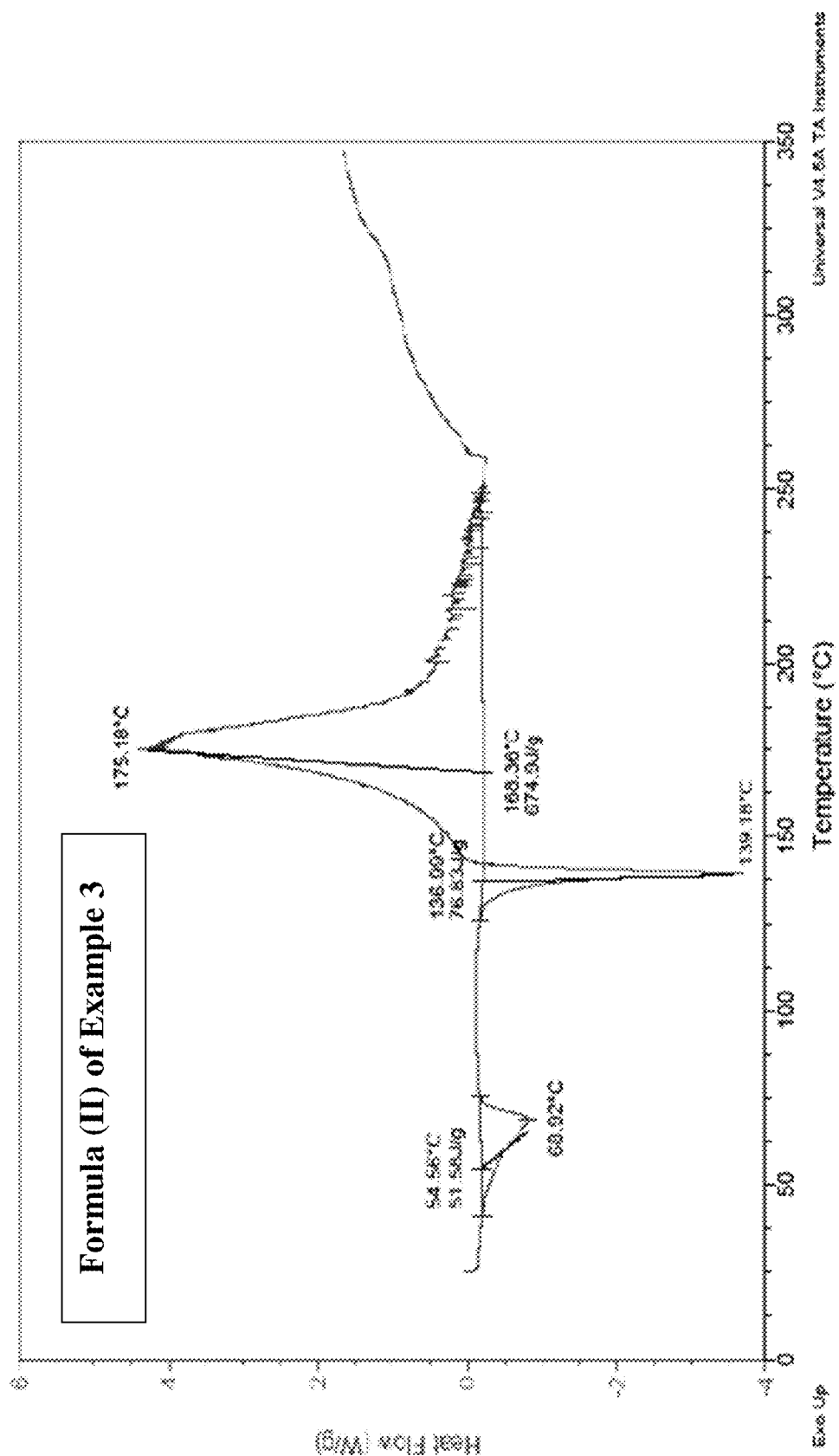
FIG. 12 depicts the differential scanning calorimetry (DSC) of Formula (II) of Example 3.

In a particular embodiment, the crystalline compound of Formula (II) is characterized by a differential scanning calorimetry thermogram substantially in accordance with FIG. 2, FIG. 7, or FIG. 12.

The compounds of the invention can be also be defined by their thermogravimetry (TG) signals. In one embodiment, the crystalline compound of Formula (II) is characterized by a thermogravimetry curve having an onset temperature of 176.07±10° C. In another embodiment, the crystalline compound of Formula (II) is characterized by a thermogravimetry curve having an onset temperature of about 176.07° C. In another embodiment, the crystalline compound of Formula (II) is characterized by a thermogravimetry curve having an onset temperature of about 175.78° C. In another embodiment, the crystalline compound of Formula (II) is characterized by a thermogravimetry curve having an onset temperature of about 159.72° C.

In another embodiment, the crystalline compound of Formula (II) is characterized by a thermo gravimetric analysis having a weight loss of 0-6% upon heating from 30±10° C. to 150±10° C. In one particular embodiment, the thermo gravimetric analysis depicts a weight loss of about 1.36% upon heating from 30° C. to 150° C. In one particular embodiment, the thermo gravimetric analysis depicts a weight loss of about 1.36% upon heating from 30° C. to 150° C. In another particular embodiment, the thermo gravimetric analysis depicts a weight loss of about 5.423% upon heating from 30° C. to 140° C.

Figure 3:
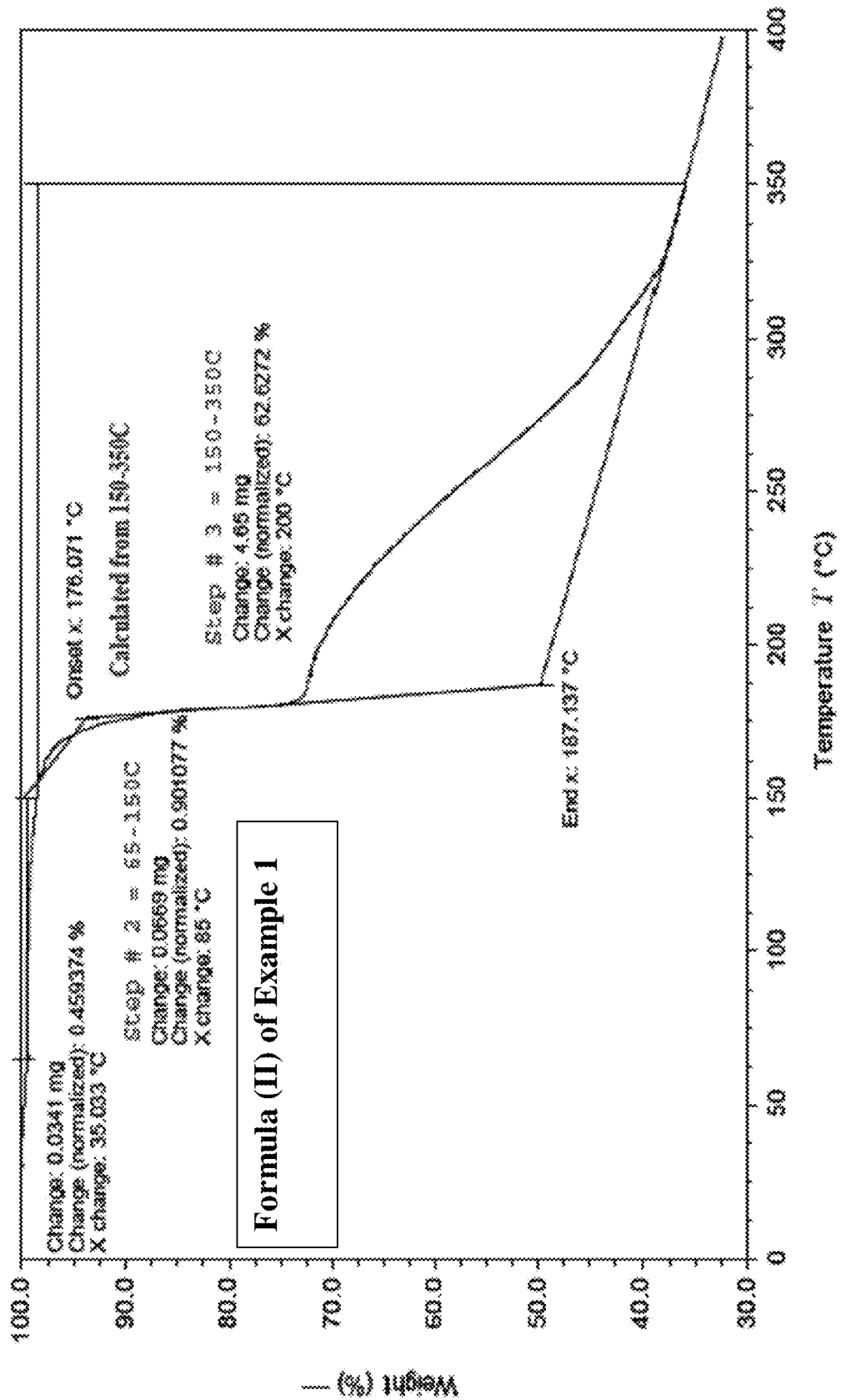
FIG. 3 depicts the thermogravimetry curve of Formula (II) of Example 1.
Figure 4:
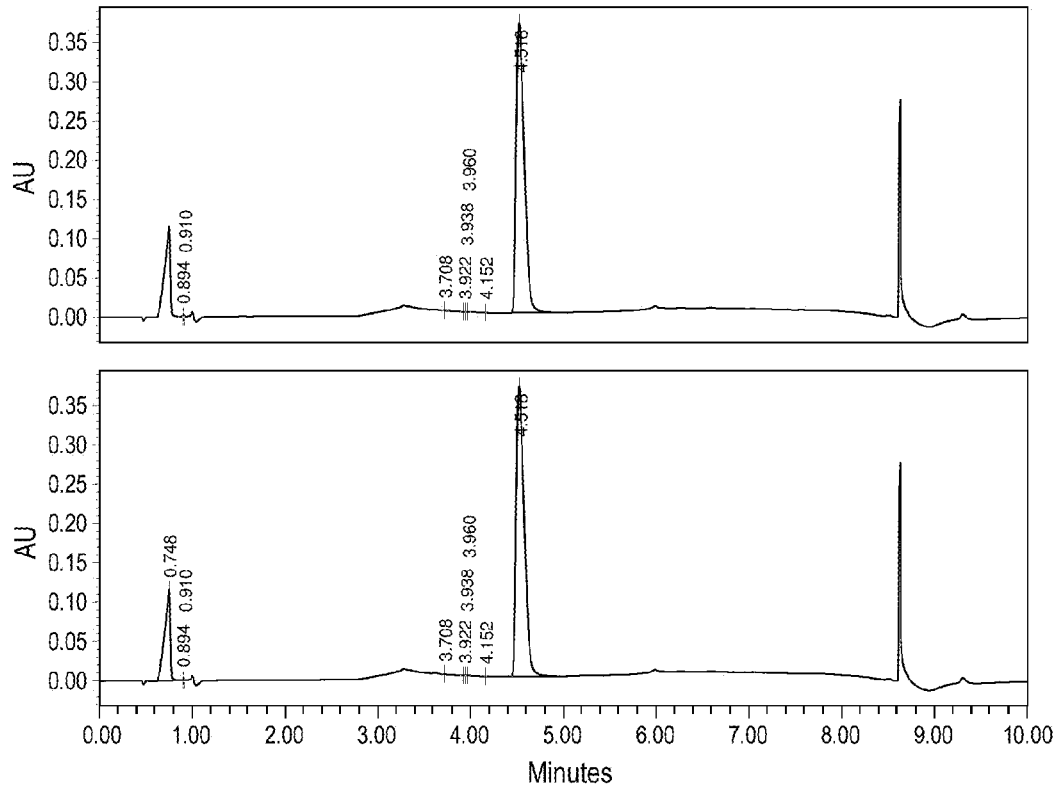
FIG. 4 depicts the HPLC chromatogram and peak areas of Formula (II) of Example 1 obtained using the HPLC method 3 of FIG. 18.
Figure 5:
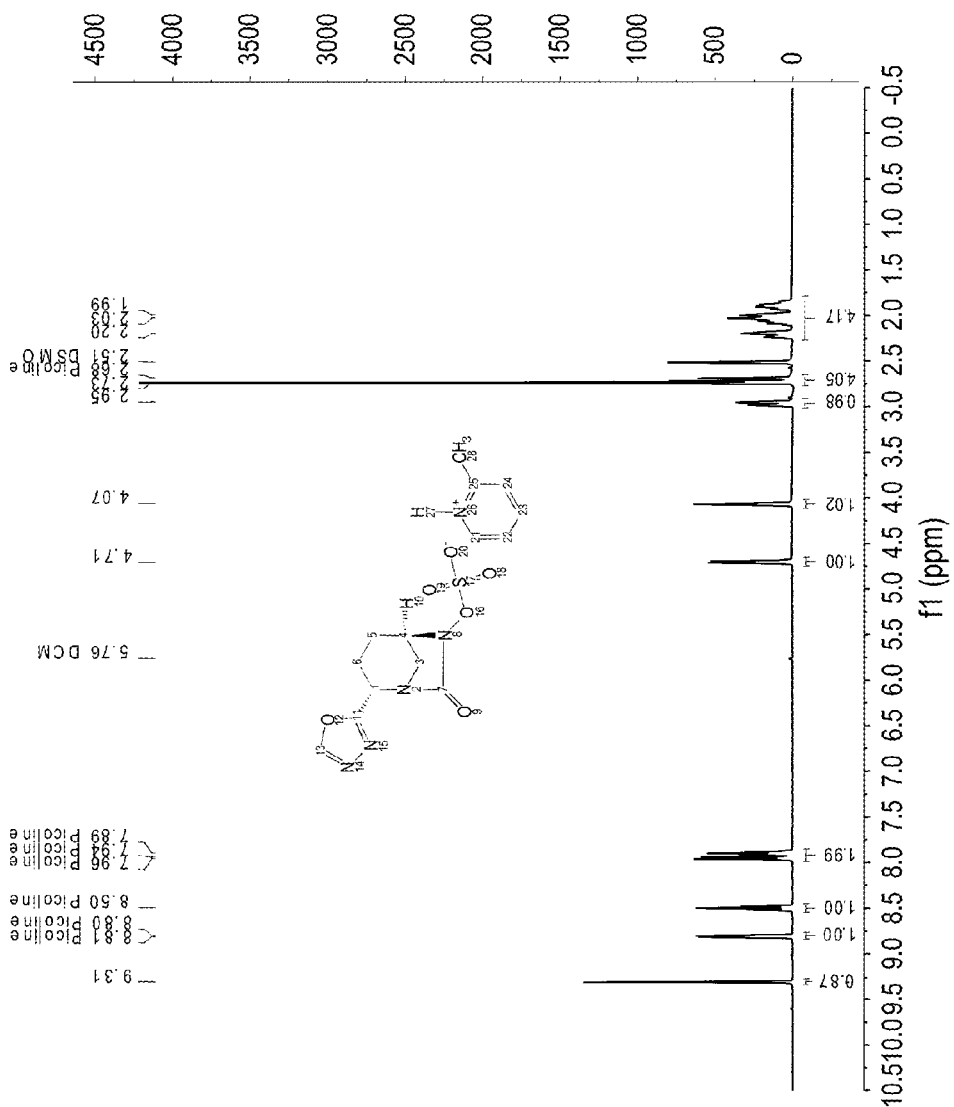
FIG. 5 depicts the $^1$H-NMR spectrum of Formula (II) of Example 1.
Figure 6:
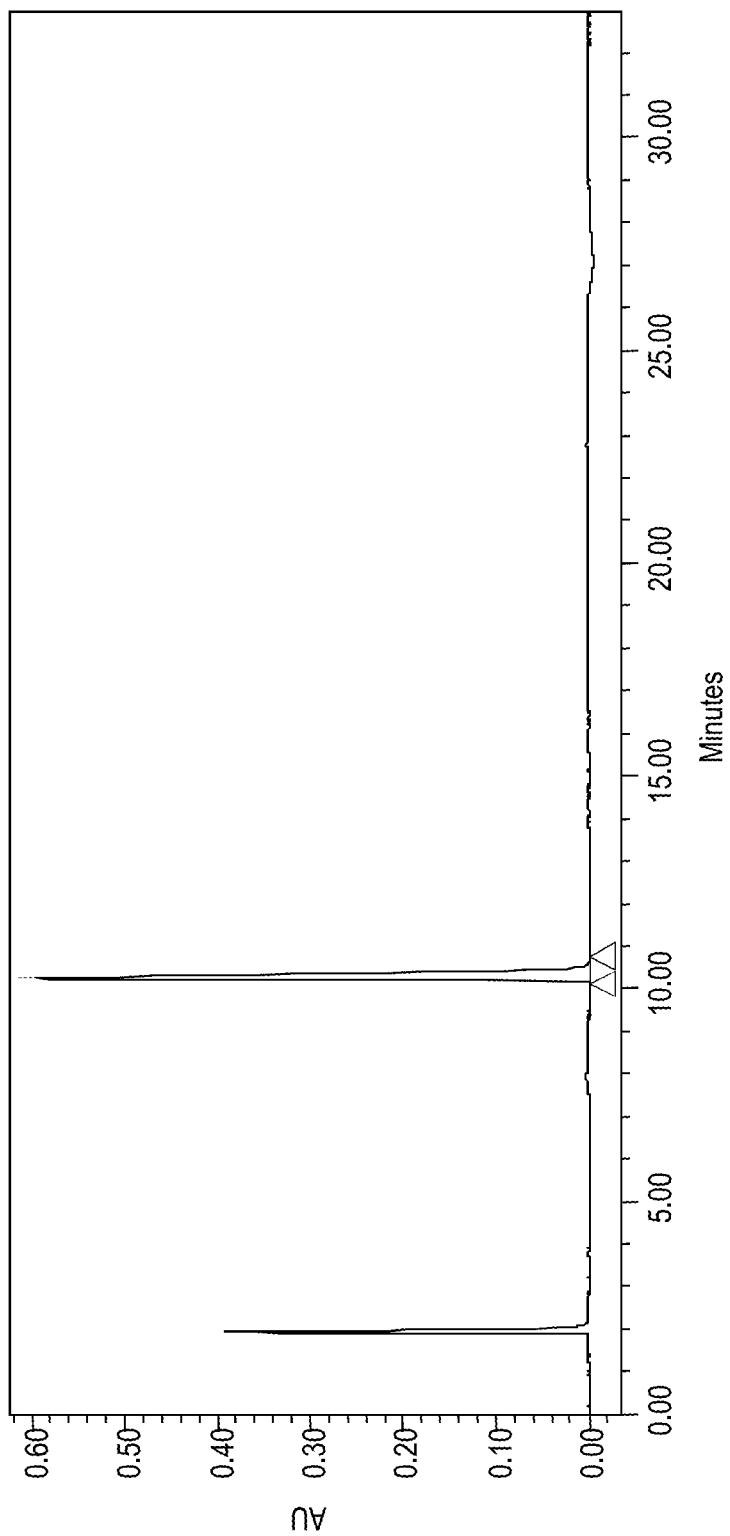
FIG. 6 depicts the HPLC chromatogram of Formula (II) of Example 1 obtained using the HPLC method 1 of FIG. 18.
Figure 8:
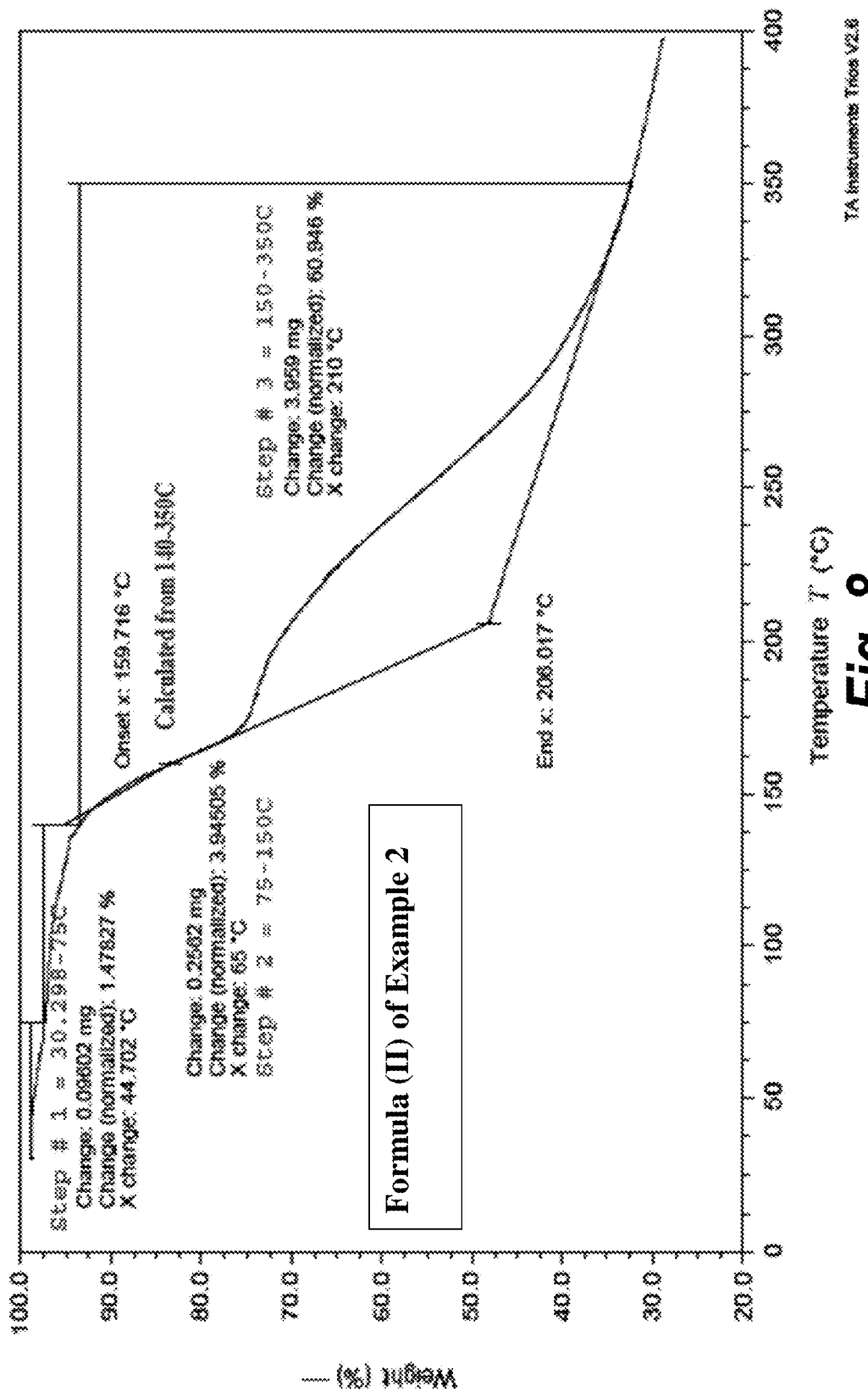
FIG. 8 depicts the thermogravimetry curve of Formula (II) of Example 2.
Figure 9:
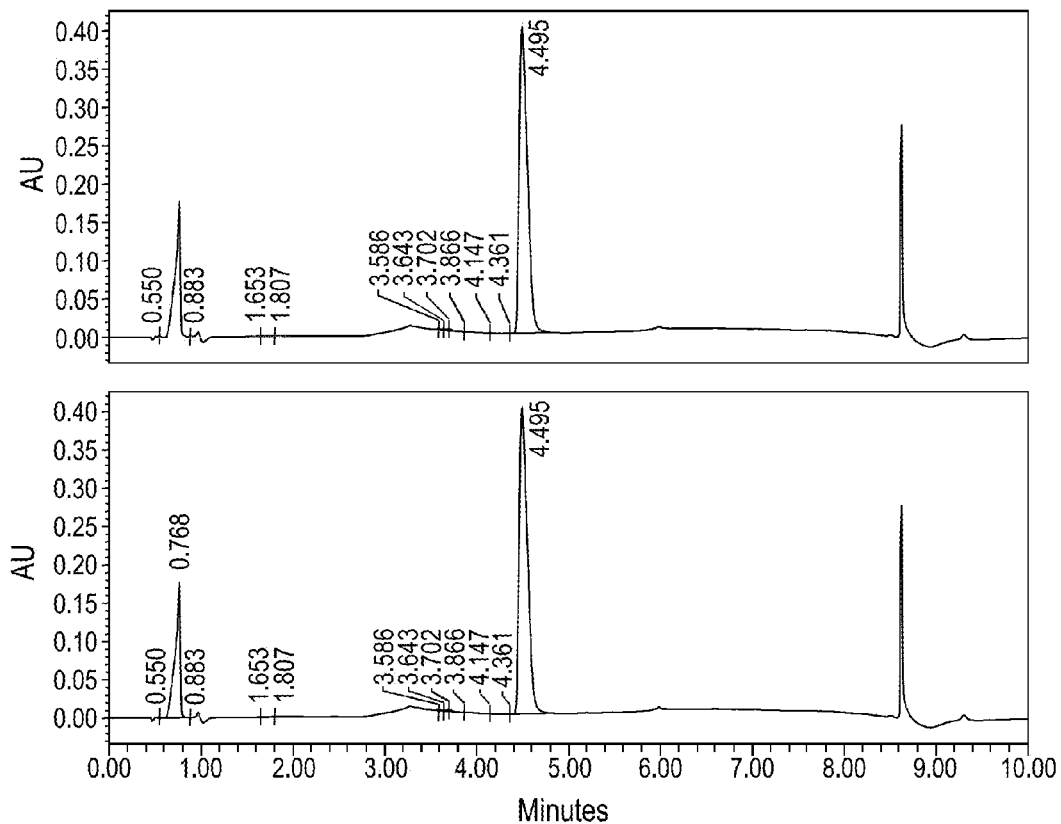
FIG. 9 depicts the HPLC chromatogram and peak areas of Formula (II) of Example 2 obtained using the HPLC method 3 of FIG. 18.
Figure 10:
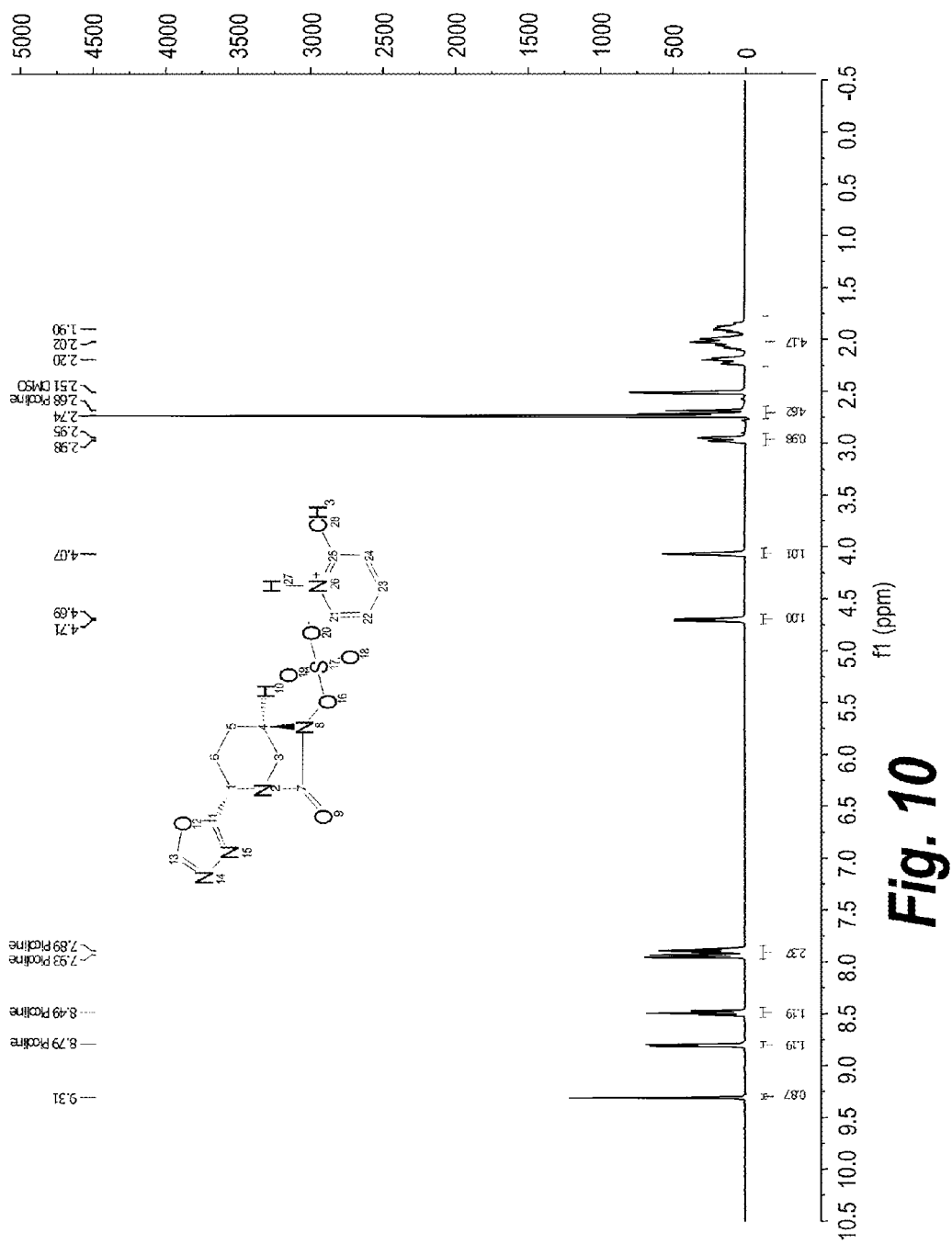
FIG. 10 depicts the $^1$H-NMR spectrum of Formula (II) of Example 2.
Figure 11:
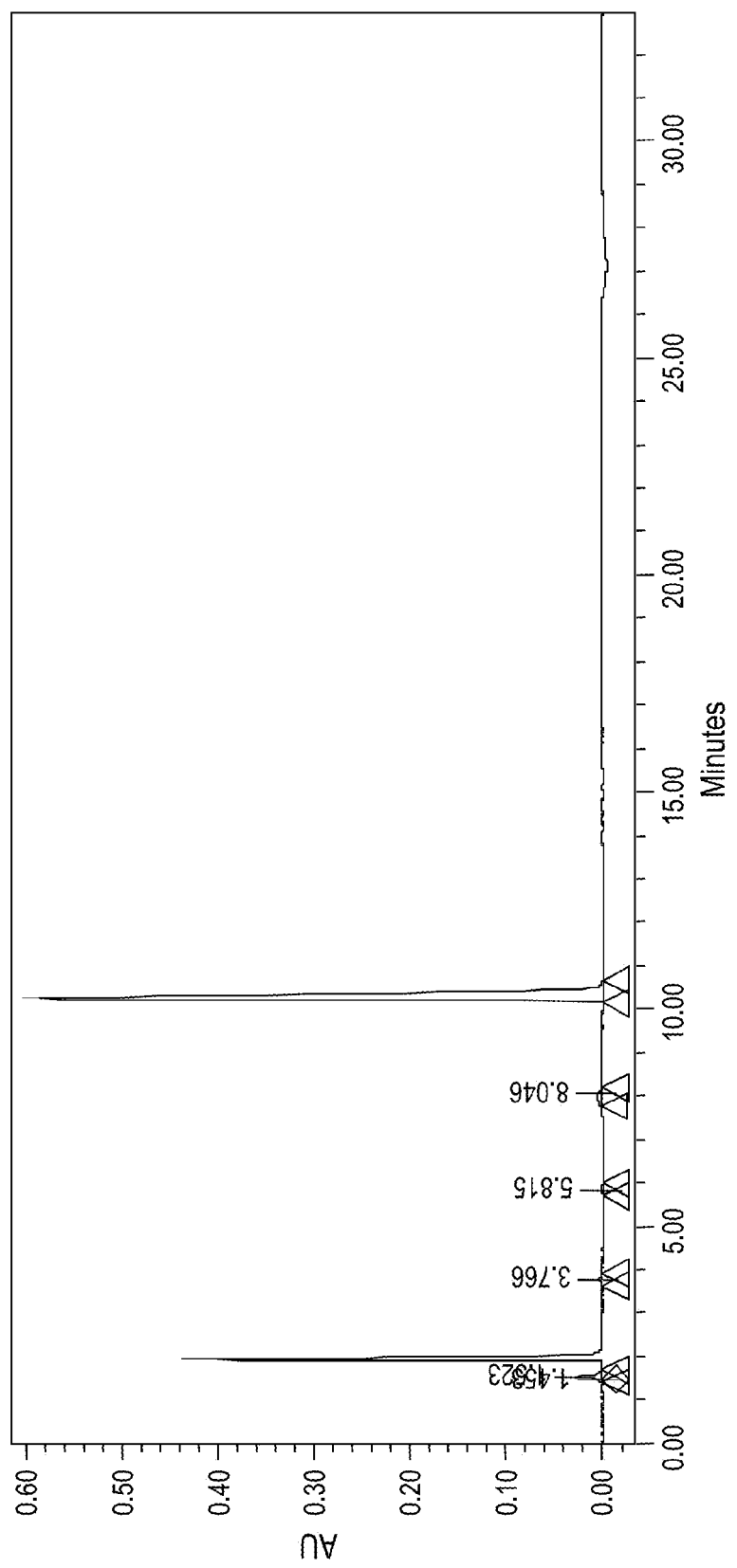
FIG. 11 depicts the HPLC chromatogram of Formula (II) of Example 2 obtained using the HPLC method 1 of FIG. 18.
Figure 13:
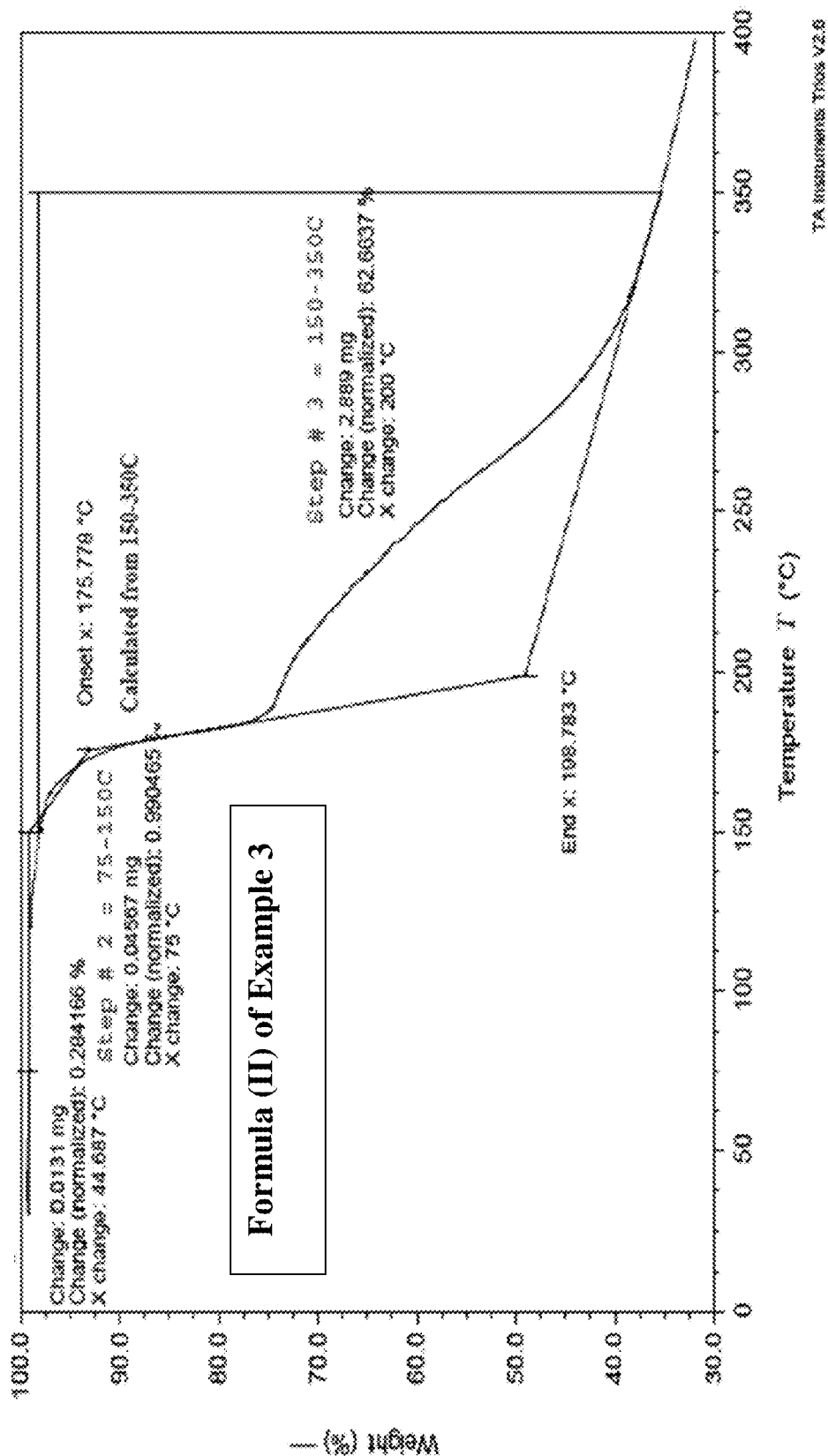
FIG. 13 depicts the thermogravimetry curve of Formula (II) of Example 3.

In a particular embodiment, the crystalline compound of Formula (II) is characterized by a thermo gravimetric analysis substantially in accordance with FIG. 3, FIG. 8, and FIG. 13.

In certain embodiments the crystalline compound of Formula (II) can comprise impurities. Non-limiting examples of impurities include undesired polymorph forms, or residual organic and inorganic molecules such as solvents, water or salts. In one embodiment, the crystalline compound of Formula (II) is substantially free from impurities. In another embodiment, the crystalline compound of Formula (II) comprises less than 10% by weight total impurities. In another embodiment, provided herein is the crystalline compound of Formula (II) comprises less than 5% by weight total impurities. In another embodiment, the crystalline compound of Formula (II) comprises less than 1% by weight total impurities. In yet another embodiment, the crystalline compound of Formula (II) comprises less than 0.1% by weight total impurities.

In another embodiment, provided herein is the crystalline compound of Formula (II) that is substantially free from amorphous compound of Formula (II). As used herein, the term "substantially free from amorphous compound of Formula (II)" means that the crystalline compound of Formula (II) contains no significant amount of amorphous compound of Formula (II). In certain embodiments, at least about 95% by weight of the crystalline compound of Formula (II) is present. In still other embodiments of the invention, at least about 99% by weight of the crystalline compound of Formula (II) is present.

In another embodiment, provided herein is the crystalline compound of Formula (II) substantially free from other crystalline forms of the compound of Formula (II). As used herein, the term "substantially free from other crystalline forms of the compound of Formula (II)" means that the crystalline compound of Formula (II) contains no significant amount of other crystalline forms of the compound of Formula (II). In certain embodiments, at least about 95% by weight of the crystalline compound of Formula (II) is present. In still other embodiments, at least about 99% by weight of the crystalline compound of Formula (II) is present.

Processes and Methods

In one aspect, provided herein is a method of making a compound of Formula (III), the method comprising the steps of:

a) reacting a compound of Formula (I) with a 2-picoline/sulfur trioxide complex in a solvent to form the compound of Formula (II);
b) collecting the compound of Formula (II); and
c) reacting the compound of Formula (II) with a sodium salt in a solvent to form the compound of Formula (III).

In one embodiment, the 2-picoline/sulfur trioxide complex is prepared by combining 2-picoline and chlorosulfonic acid.

In another embodiment, the solvent of step a) comprises a halogenated solvent. In a particular embodiment, the solvent of step a) comprises dichloromethane. In another embodiment, the solvent of step a) further comprises a second organic solvent. In certain embodiments, the second organic solvent is selected from ethers and esters. In a particular embodiment, the second organic solvent is tetrahydrofuran (THF).

In another embodiment, step b) comprises crystallizing the compound of Formula (II) and separating the compound of Formula (II) from the reaction mixture. In another embodiment, the sodium salt of step c) is selected from organic and inorganic salts. Non-limiting examples of sodium salts include: sodium acetate, sodium carbonate, sodium phosphate, sodium benzoate, sodium borate, sodium sulfate, and sodium bisulfate. Further non-limiting examples of sodium salts are sodium propionate, sodium butyrate, sodium pivalate, sodium hexanoate, sodium 2-ethylhexanoate, and sodium octanoate. In another embodiment, the solvent of step c) comprises water. In still another embodiment, the solvent of step c) further comprises a water-miscible organic solvent. Non-limiting examples of water-miscible organic solvents include alcohols and ethers (e.g., tetrahydrofuran). In a particular embodiment, the solvent of step c) further comprises tetrahydrofuran. In another particular embodiment, the solvent of step c) further comprises isopropanol.

In another particular embodiment, the solvent of step c) comprises methyl ethyl ketone. In another particular embodiment, the solvent of step c) comprises isopropyl acetate. In another particular embodiment, the solvent of step c) comprises ethyl acetate. In an embodiment, the solvent of step c) further comprises water.

In one particular embodiment, provided herein is a method for preparing a compound of Formula (III), the method comprising the steps of:

a) reacting a compound of Formula (I):

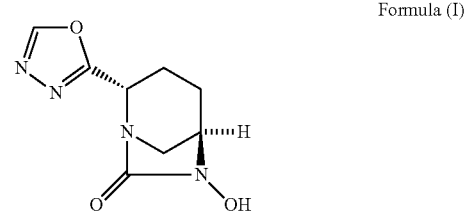 [SMILES: O=C1N(O)[C@@H]2CC[C@@H](c3nnco3)N1C2]

Formula (I)

with a 2-picoline/sulfur trioxide complex in dichloromethane to form the crystalline compound of Formula (II):

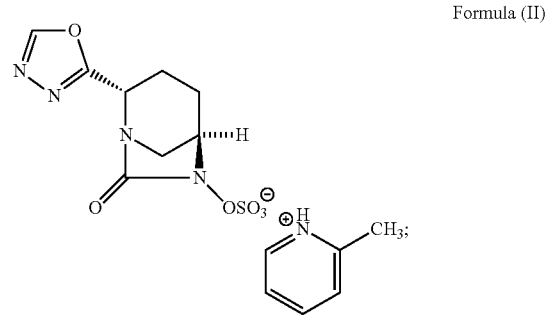

Formula (II)

b) collecting the crystalline compound of Formula (II); and
c) reacting the crystalline compound of Formula (II) with sodium bicarbonate in water to form the sodium salt of Formula (III):

Formula (III)

[Structure: oxadiazole-piperidine with N-C(=O) and OSO₃Na substituent]

The 2-picoline/sulfur trioxide complex can be obtained by various methods prior to being reacted with the compound of Formula (I). In one particular embodiment, the 2-picoline/sulfur trioxide complex is prepared by reacting 2-picoline and chlorosulfonic acid in a solvent. In one embodiment, the solvent is dichloromethane. In another embodiment, the picoline and chlorosulfonic acid are reacted at a molar ratio of about 2:1. In another embodiment, the picoline-sulfur trioxide complex is prepared less than 2 hours, less than 1.5 hours, less than 1 hour, or less than 30 minutes prior to being reacted with the compound of Formula (I). In still another embodiment, the picoline-sulfur trioxide complex is prepared about 30 minutes prior to being reacted with the compound of Formula (I).

In another particular embodiment, provided herein is a method for preparing a compound of Formula (III), the method comprising the steps of:

a) reacting a compound of Formula (I):

Formula (I)

[Structure: oxadiazole-piperidine with N-C(=O) and OH substituent]

with a 2-picoline/sulfur trioxide complex in dichloromethane to form the crystalline compound of Formula (II):

Formula (II)

[Structure: oxadiazole-piperidine with N-C(=O) and OSO₃⁻ with protonated 2-methylpyridinium counterion]

b) collecting the crystalline compound of Formula (II); and c) reacting the crystalline compound of Formula (II) with sodium 2-ethylhexanoate in a solvent comprising isopropyl acetate to form the sodium salt of Formula (III):

Formula (III)

[Structure: oxadiazole-piperidine with N-C(=O) and OSO₃Na substituent]

In an embodiment, step c) further comprises water.

The 2-picoline/sulfur trioxide complex can be obtained by various methods prior to being reacted with the compound of Formula (I). In one particular embodiment, the 2-picoline/sulfur trioxide complex is prepared by reacting 2-picoline and chlorosulfonic acid in a solvent. In one embodiment, the solvent is dichloromethane. In another embodiment, the picoline and chlorosulfonic acid are reacted at a molar ratio of about 2:1. In another embodiment, the picoline-sulfur trioxide complex is prepared less than 2 hours, less than 1.5 hours, less than 1 hour, or less than 30 minutes prior to being reacted with the compound of Formula (I). In still another embodiment, the picoline-sulfur trioxide complex is prepared about 30 minutes prior to being reacted with the compound of Formula (I).

In another aspect, provided herein is a method of making a compound of Formula (III), the method comprising the steps of:

a) reacting a compound of Formula (I) with 3-picoline/sulfur trioxide complex in a solvent to form the compound of Formula (IIa);

b) collecting the compound of Formula (IIa); and c) reacting the compound of Formula (IIa) with a sodium salt in a solvent to form the compound of Formula (III).

In an embodiment, the 3-picoline/sulfur trioxide complex is prepared by combining 3-picoline and chlorosulfonic acid.

In another aspect, provided herein is a method of making a compound of Formula (III), the method comprising the steps of:

a) reacting a compound of Formula (I) with a 4-picoline/sulfur trioxide complex in a solvent to form the compound of Formula (IIb);

b) collecting the compound of Formula (IIb); and c) reacting the compound of Formula (IIb) with a sodium salt in a solvent to form the compound of Formula (III).

In an embodiment, the 4-picoline/sulfur trioxide complex is prepared by combining 3-picoline and chlorosulfonic acid.

EXAMPLES

Example 1

Small Scale Synthesis of 2-Methylpyridin-1-ium (2S,5R)-2-(1,3,4-oxadiazol-2-yl)-7-oxo-1,6-diazabicyclo[3.2.1]octan-6-yl sulfate (Formula (II))

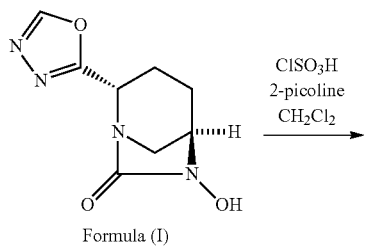

Step 1. Preparation of 2-Picoline/Sulfur Trioxide Complex (Reagent Formation)

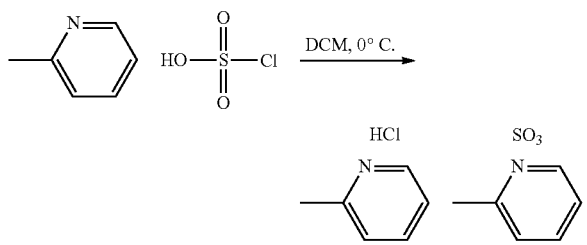

In a 50 ml 3-neck RBF equipped with a magnetic stir bar, thermocouple probe, addition funnel, nitrogen inlet adapter, and a rubber septum, charged dichloromethane (anh) (2.5 ml) and 2-picoline (1.46 ml, 14.7 mmol). This picoline solution was chilled in an ice/NaCl bath to −2° C. Then a solution of chlorosulfonic acid (0.478 ml, 7.14 mmol) in dichloromethane (anh) (2.5 ml) was added slowly, with temp being maintained below 5° C. (addition time=30 min). The resulting orange solution was stirred for 30 minutes before being added to the sulfation reaction at room temperature as described in this Example, step 2 (below).

Step 2. Preparation of 2-methylpyridin-1-ium (2S,5R)-2-(1,3,4-oxadiazol-2-yl)-7-oxo-1,6-diazabicyclo[3.2.1]octan-6-yl sulfate (Sulfation)

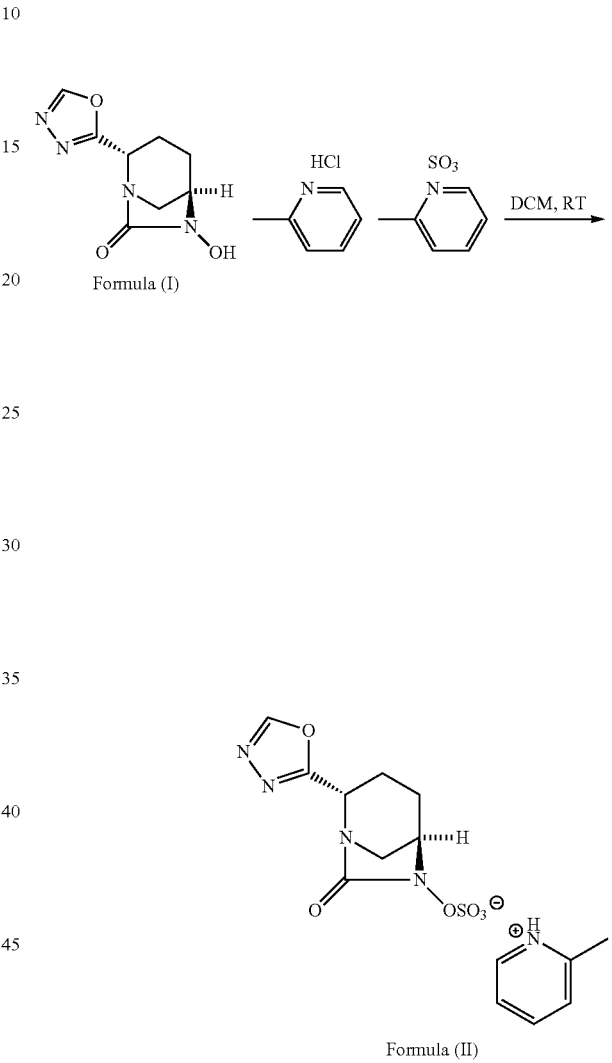

To a 20 mL scintillation with a nitrogen needle, rubber septum and a magnetic stir bar containing (2S,5R)-6-hydroxy-2-(1,3,4-oxadiazol-2-yl)-1,6-diazabicyclo[3.2.1]octan-7-one (Formula (I)) (1.00 g, 4.76 mmol) was charged dichloromethane (5.00 ml) and stirred at room temperature. The 2-picoline/SO₃ complex in dichloromethane prepared according to this Example, step 1, was added and the reaction mixture was stirred at room temperature for 15 hours.

The reaction mixture was cooled in an ice bath for 1 hour. Then solid precipitates were filtered off and washed with 5 ml of cold dichloromethane to give a nice, white powder that was dried under high vacuum overnight at room temperature, providing 2-methylpyridin-1-ium (2S,5R)-2-(1,3,4-oxadiazol-2-yl)-7-oxo-1,6-diazabicyclo[3.2.1]octan-6-yl sulfate (Formula (II)) (1.1458 g, Yield: 63%).

XRPD and DSC data showed that the product is in crystalline form (FIGS. 1 and 2). The product was also analyzed by TGA, NMR, and HPLC (FIGS. 3-6).

Example 1B

Synthesis of 3-Methylpyridin-1-ium (2S,5R)-2-(1,3,4-oxadiazol-2-yl)-7-oxo-1,6-diazabicyclo[3.2.1]octan-6-yl sulfate (Formula (IIa)) (Prophetic)

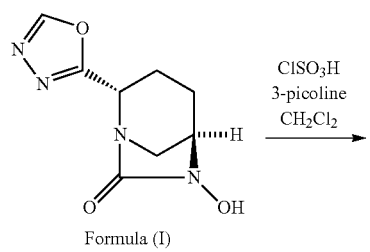

Formula (I)

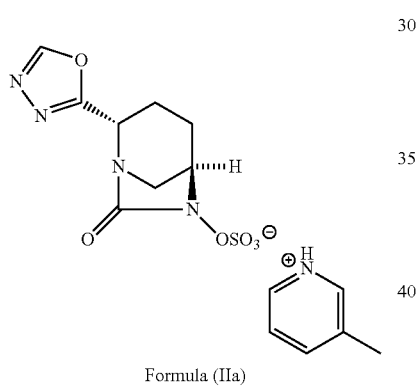

Formula (IIa)

Step 1. Preparation of 3-Picoline/Sulfur Trioxide Complex (Reagent Formation)

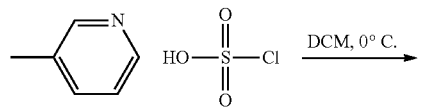

Same as Example 1, step 1, substituting 3-picoline for 2-picoline.

Step 2. Preparation of 3-methylpyridin-1-ium (2S, 5R)-2-(1,3,4-oxadiazol-2-yl)-7-oxo-1,6-diazabicyclo[3.2.1]octan-6-yl sulfate (Sulfation)

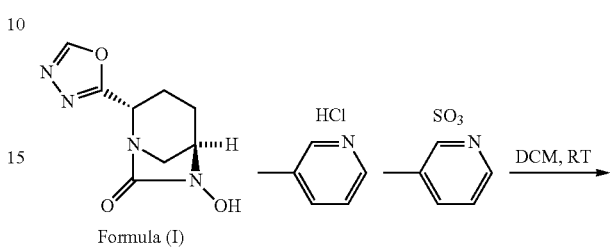

Formula (I)

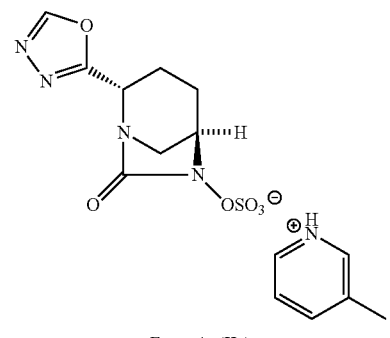

Formula (IIa)

Same as Example 1, step 2, substituting the 3-picoline-SO₃ complex in DCM prepared according to this Example, step 1.

Example 1C

Synthesis of 4-Methylpyridin-1-ium (2S,5R)-2-(1,3,4-oxadiazol-2-yl)-7-oxo-1,6-diazabicyclo[3.2.1]octan-6-yl sulfate (Formula (IIb)) (Prophetic)

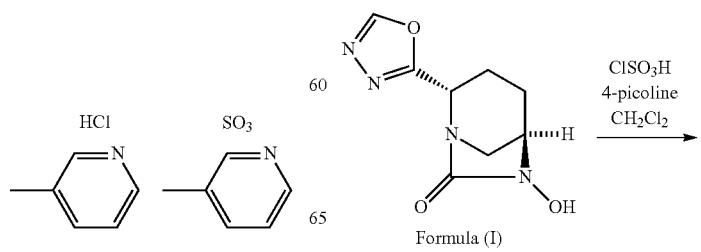

Formula (I)

17

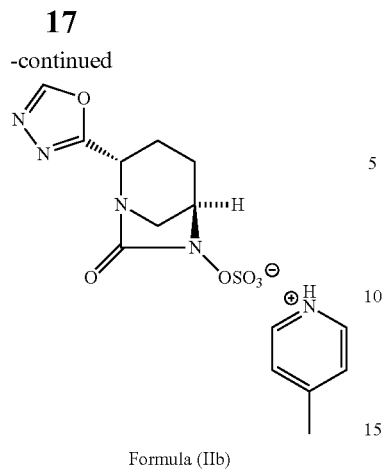

Formula (IIb)

Step 1. Preparation of 4-Picoline/Sulfur Trioxide Complex (Reagent Formation)

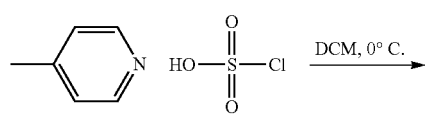

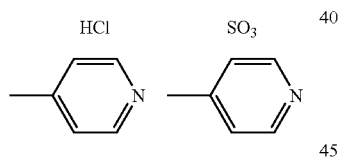

Same as Example 1, Step 1, substituting 4-picoline for 2-picoline.

Step 2. Preparation of 4-methylpyridin-1-ium (2S, 5R)-2-(1,3,4-oxadiazol-2-yl)-7-oxo-1,6-diazabicyclo[3.2.1]octan-6-yl sulfate (Sulfation)

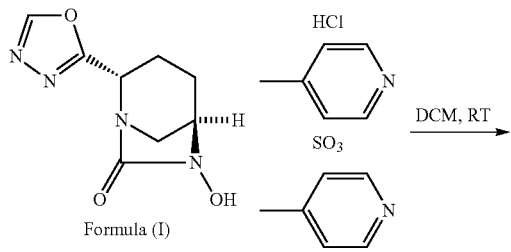

18

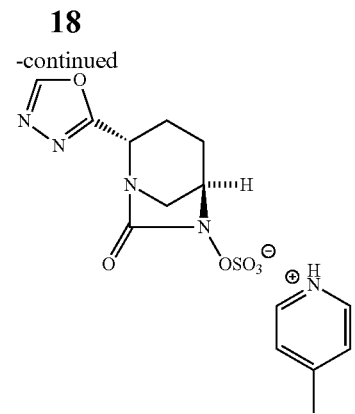

Formula (IIb)

Same as Example 1, step 2, substituting the 4-picoline-SO₃ complex in DCM prepared according to this Example, step 1.

Example 2

Small Scale Synthesis of 2-Methylpyridin-1-ium (2S,5R)-2-(1,3,4-oxadiazol-2-yl)-7-oxo-1,6-diazabicyclo[3.2.1]octan-6-yl sulfate (with Anti-Solvent)

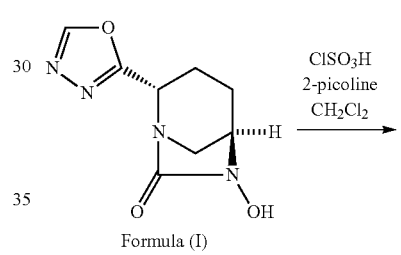

Formula (I)

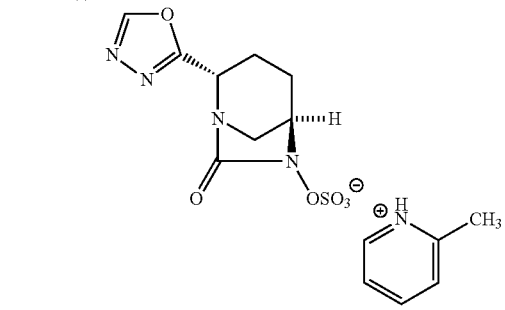

Formula (II)

Step 1. Preparation of Picoline-Sulfur Trioxide Complex (Reagent Formation)

In a 50 ml 3-neck RBF equipped with a magnetic stir bar, thermocouple probe, addition funnel, nitrogen inlet adapter, and a rubber septum, charged dichloromethane (anh) (2.5 ml) and 2-picoline (1.46 ml, 14.7 mmol). This 2-picoline solution was chilled in an ice/NaCl bath to −2° C. Then a solution of chlorosulfonic acid (0.478 ml, 7.14 mmol) in dichloromethane (anh) (2.5 ml) was added over 30 minutes, with the temperature being maintained below 5° C. The resulting orange solution was stirred for 30 minutes before being added to the sulfation reaction at room temperature as described in this Example, step 2.

Step 2. Preparation of 2-methylpyridin-1-ium (2S, 5R)-2-(1,3,4-oxadiazol-2-yl)-7-oxo-1,6-diazabicyclo [3.2.1]octan-6-yl sulfate (Sulfation)

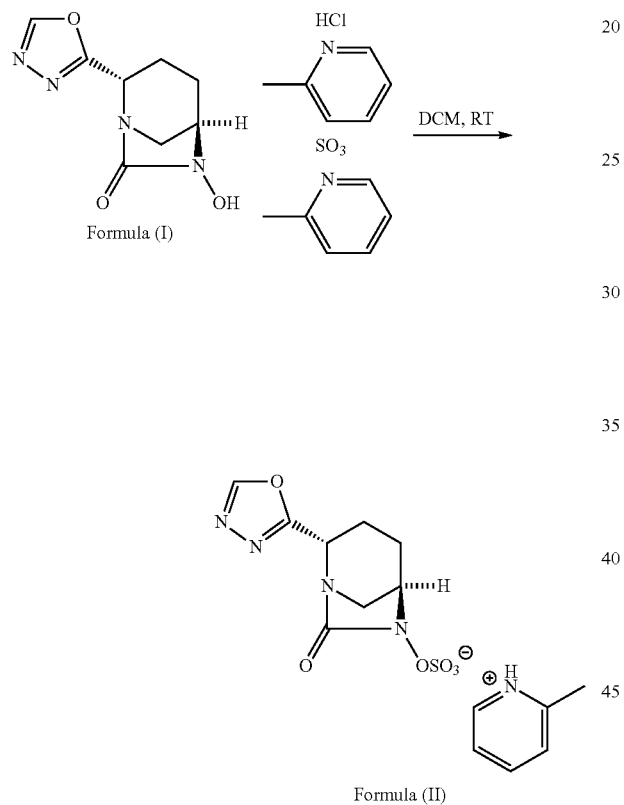

To a 20 mL scintillation with a nitrogen needle, rubber septum and a magnetic stir bar containing (2S,5R)-6-hydroxy-2-(1,3,4-oxadiazol-2-yl)-1,6-diazabicyclo[3.2.1]octan-7-one (Formula (I)) (1.00 g, 4.76 mmol) was charged dichloromethane (5.00 ml) and stirred to at RT. The 2-picoline/SO$_3$ complex in dichloromethane prepared according to this Example, step 1, was added and the reaction mixture was stirred at room temperature for 15 hours.

5 ml THF (anti-solvent) was added to the reaction mixture over 30 seconds. The reaction mixture was cooled in an ice bath for 1 h. Then solid precipitates were filtered off, washed with 5 ml of cold mixture of 2:1 DCM/THF (v/v), and dried under high vacuum overnight at room temperature, providing 2-methylpyridin-1-ium (2S,5R)-2-(1,3,4-oxadiazol-2-yl)-7-oxo-1,6-diazabicyclo[3.2.1]octan-6-yl sulfate (Formula (II)) (1.7455 g, Yield: 96%).

XRPD and DSC data showed that the product was in crystalline form (FIGS. 1 and 7). The product was also analyzed by TGA, NMR and HPLC (FIGS. 8-11).

Example 3

Scale up of Synthesis of 2-methylpyridin-1-ium (2S, 5R)-2-(1,3,4-oxadiazol-2-yl)-7-oxo-1,6-diazabicyclo [3.2.1]octan-6-yl sulfate (No Anti-Solvent)

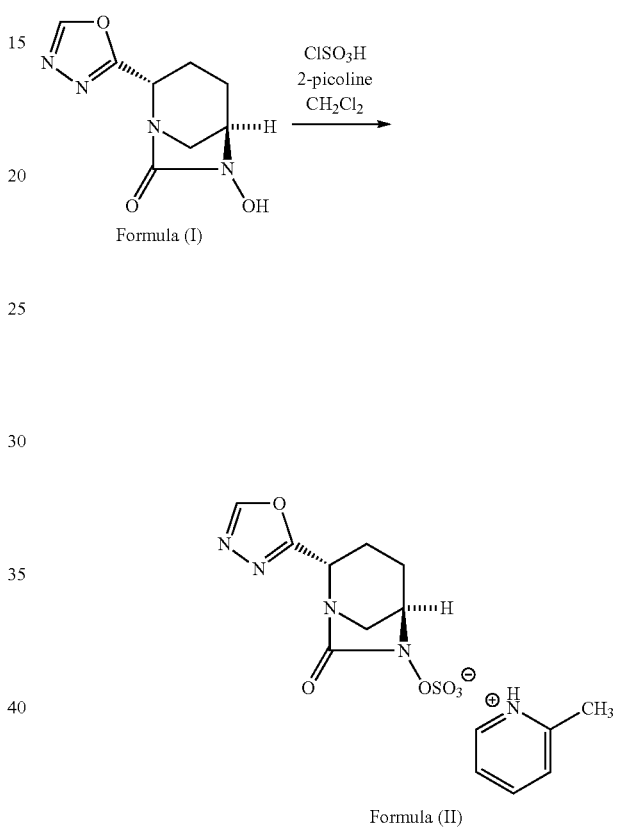

A suspension of Formula (I) (7.35 g, 30 mmol, mixed lots) in CH$_2$Cl$_2$ (73.5 mL) was prepared in a RBF. In a second RBF, a solution of 2-picoline (10.73 mL, 3.1 eq) in CH$_2$Cl$_2$ (37 mL) was cooled to between −10 and −5° C. A solution of chlorosulfonic acid (6.01 mL, 1.5 eq in 37 mL of CH$_2$Cl$_2$) was added to the 2-picoline solution at such a rate that reaction temperature did not exceed 10° C. After stirring between 0-10° C. for 30 min, the clear, colorless solution was transferred into the suspension of Formula (I) over ~15 min at room temperature. The reaction was monitored by HPLC and deemed complete after stirring at RT for ~6 h. During this time, the clear solution slowly became cloudy before becoming thick slurry. The reaction mixture was stirred for 16 h. HPLC showed that the reaction was complete. The excess CH$_2$Cl$_2$ was distilled out under vacuum at room temperature to a final volume of ~45-50 mL. The suspension was stirred at RT for 3 h and filtered. The cake was rinsed with cold CH$_2$Cl$_2$ (−35° C., 2×15 mL), suction dried under nitrogen at RT for 1.5 h. The white solid was dried under vacuum at RT for 24 h to afford 8.1 g of Formula (II) (Yield: 70.5%).

Figure 14:
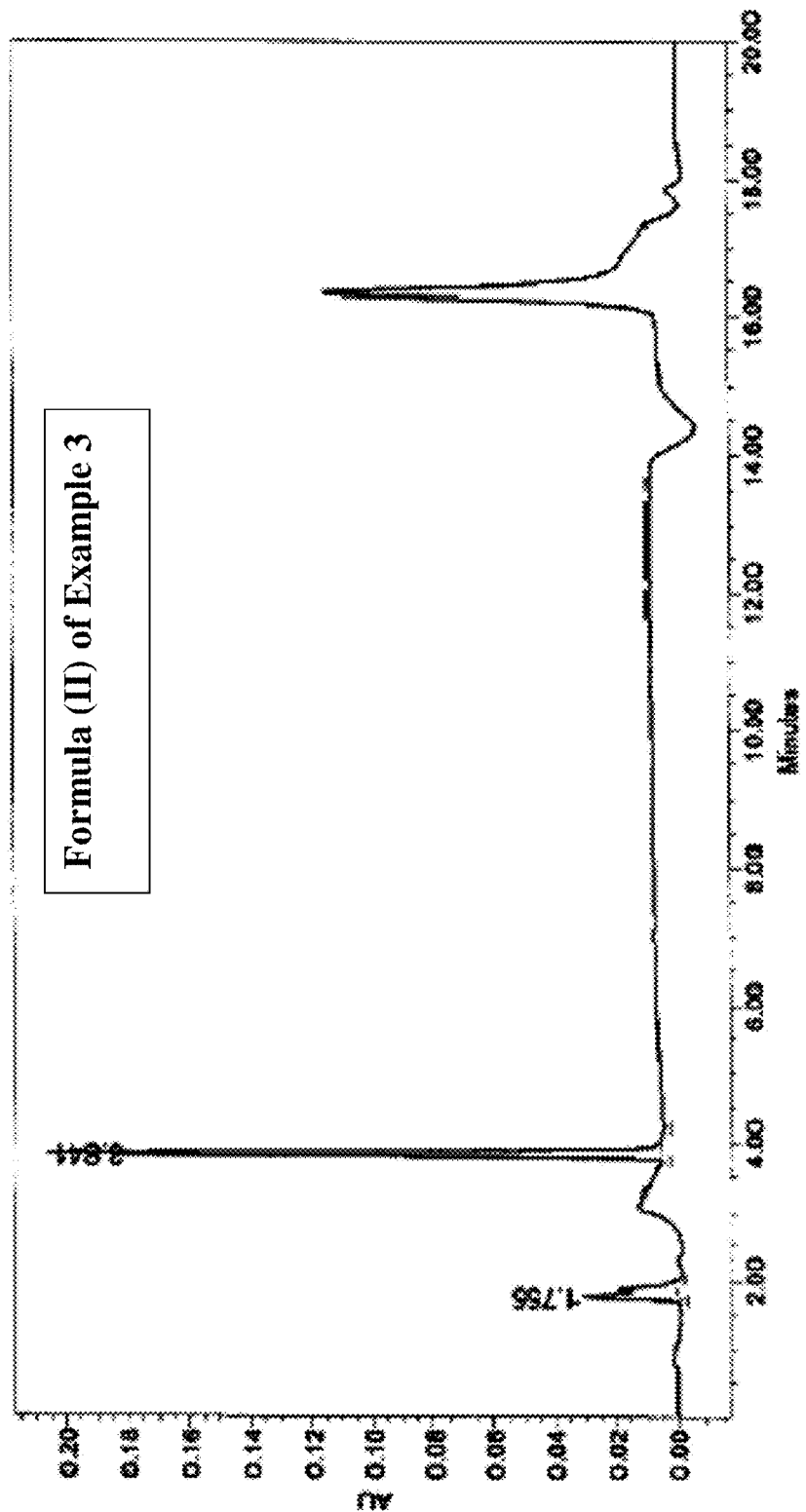
FIG. 14 depicts the HPLC chromatogram and peak areas of Formula (II) of Example 3 obtained using the HPLC method 2 of FIG. 18

XRPD and DSC data showed that the product was in crystalline form (FIGS. 1 and 12). The product was also analyzed by TGA and HPLC (FIGS. 13 and 14).

Example 4

Further Scale up of Synthesis of 2-methylpyridin-1-ium (2S,5R)-2-(1,3,4-oxadiazol-2-yl)-7-oxo-1,6-diazabicyclo[3.2.1]octan-6-yl sulfate (With Anti-Solvent)

Step 1. Preparation of Picoline-Sulfur Trioxide Complex (Reagent Formation)

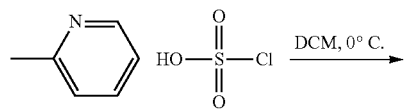

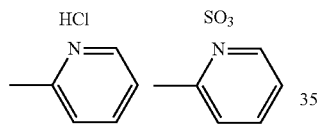

To a 100 ml 3-neck RBF equipped with a magnetic stir bar, thermocouple probe, addition funnel, nitrogen inlet adapter, and a rubber septum, was charged dichloromethane (anh) (25 ml) and 2-picoline (11.88 ml, 120 mmol). This picoline solution was chilled in an ice/NaCl bath to −3.5° C. Then a solution of chlorosulfonic acid (3.82 ml, 57.1 mmol) in dichloromethane (anh) (25 ml) was added over 50 minutes, with the temperature being maintained below 5° C. The resulting pale yellow solution was stirred for 1 h at room temperature before being added to the sulfation reaction at room temperature as described in this Example, step 2.

Step 2. Preparation of 2-methylpyridin-1-ium (2S,5R)-2-(1,3,4-oxadiazol-2-yl)-7-oxo-1,6-diazabicyclo[3.2.1]octan-6-yl sulfate (Sulfation)

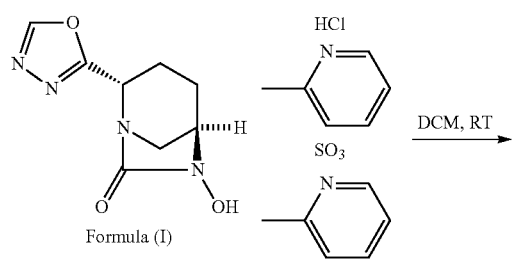

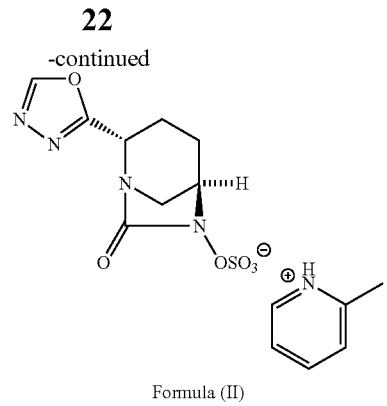

Formula (II)

To a 250 mL 3-neck RBF equipped with a magnetic stir bar, thermocouple probe, nitrogen inlet adapter, and a rubber septum containing (2S,5R)-6-hydroxy-2-(1,3,4-oxadiazol-2-yl)-1,6-diazabicyclo[3.2.1]octan-7-one (Formula (I)) (10.00 g, 47.6 mmol) was charged DCM (50.00 ml) and stirred to at RT. The picoline/SO₃ complex in DCM prepared according to this Example, step 1, was added and the reaction mixture was stirred at room temperature for 21 hours.

50 ml THF (anti-solvent) was added to the reaction mixture over 20 minutes. The reaction mixture was stirred at ambient temperature for 30 minutes before being cooled in an ice bath for 1.25 h. Then solid precipitates were filtered off, washed with 50 ml of cold mixture of 2:1 DCM/THF (v/v), and dried under high vacuum overnight at room temperature, providing 2-methylpyridin-1-ium (2S,5R)-2-(1,3,4-oxadiazol-2-yl)-7-oxo-1,6-diazabicyclo[3.2.1]octan-6-yl sulfate (Formula (II), Batch 4) (16.06 g, 41.9 mmol, Yield: 88%).

Figure 15:
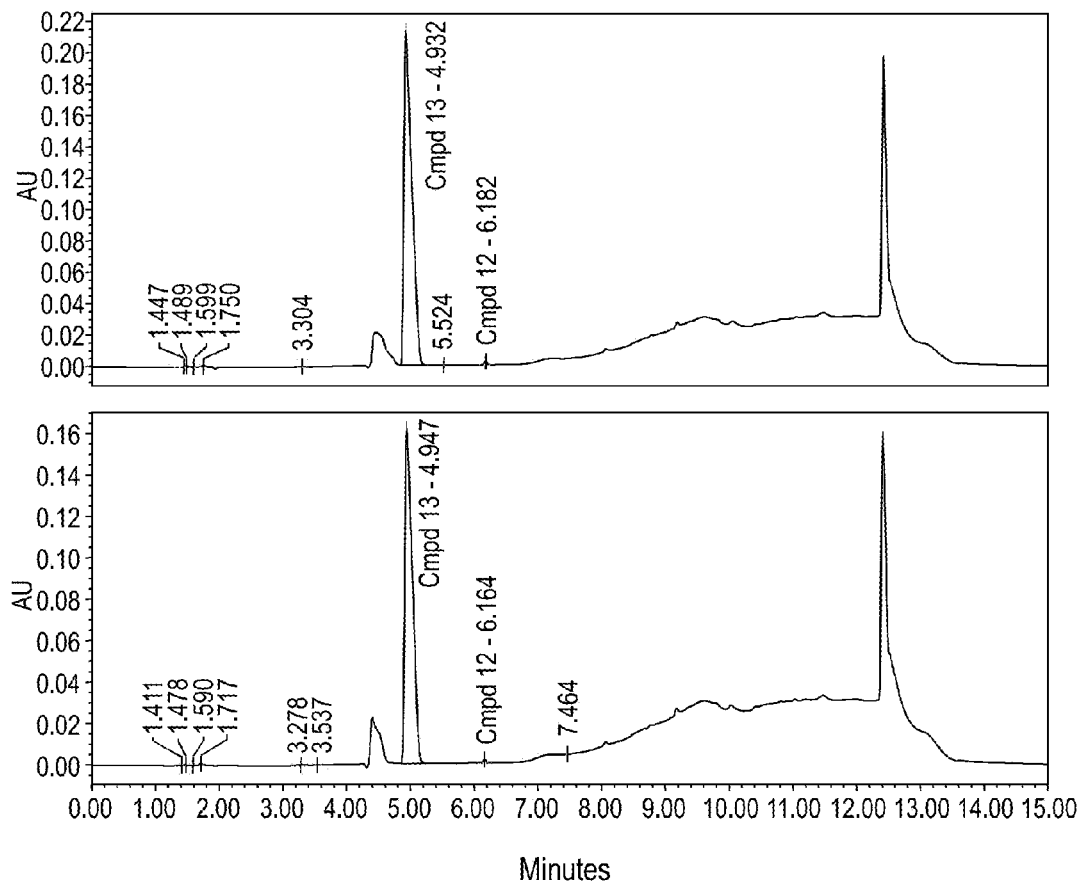
FIG. 15 depicts the HPLC chromatogram and peak areas of Formula (II) of Example 4 obtained using the HPLC method 4 of FIG. 18.
Figure 16:
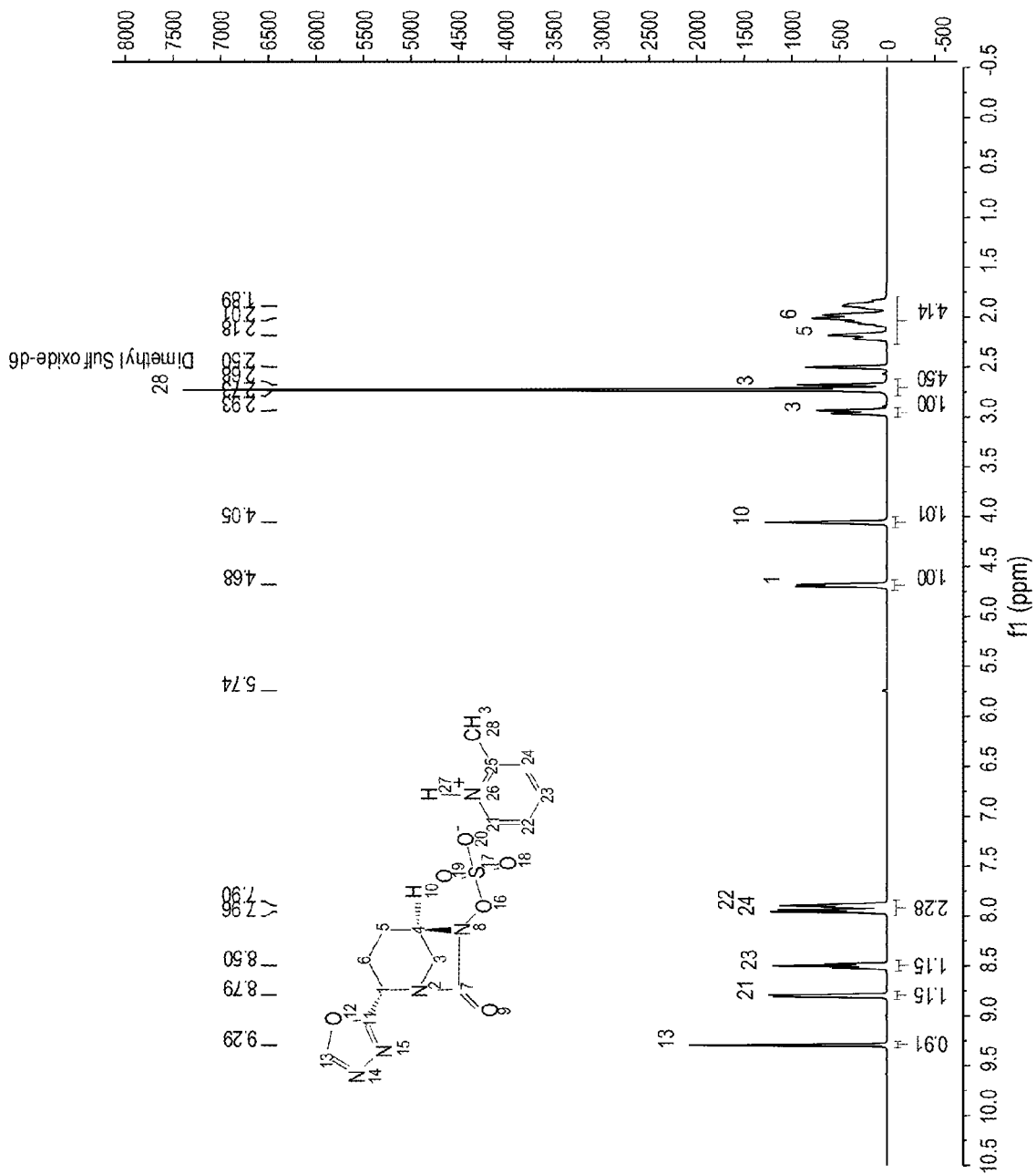
FIG. 16 depicts the $^1$H-NMR spectrum of Formula (II) of Example 4.
Figure 17:
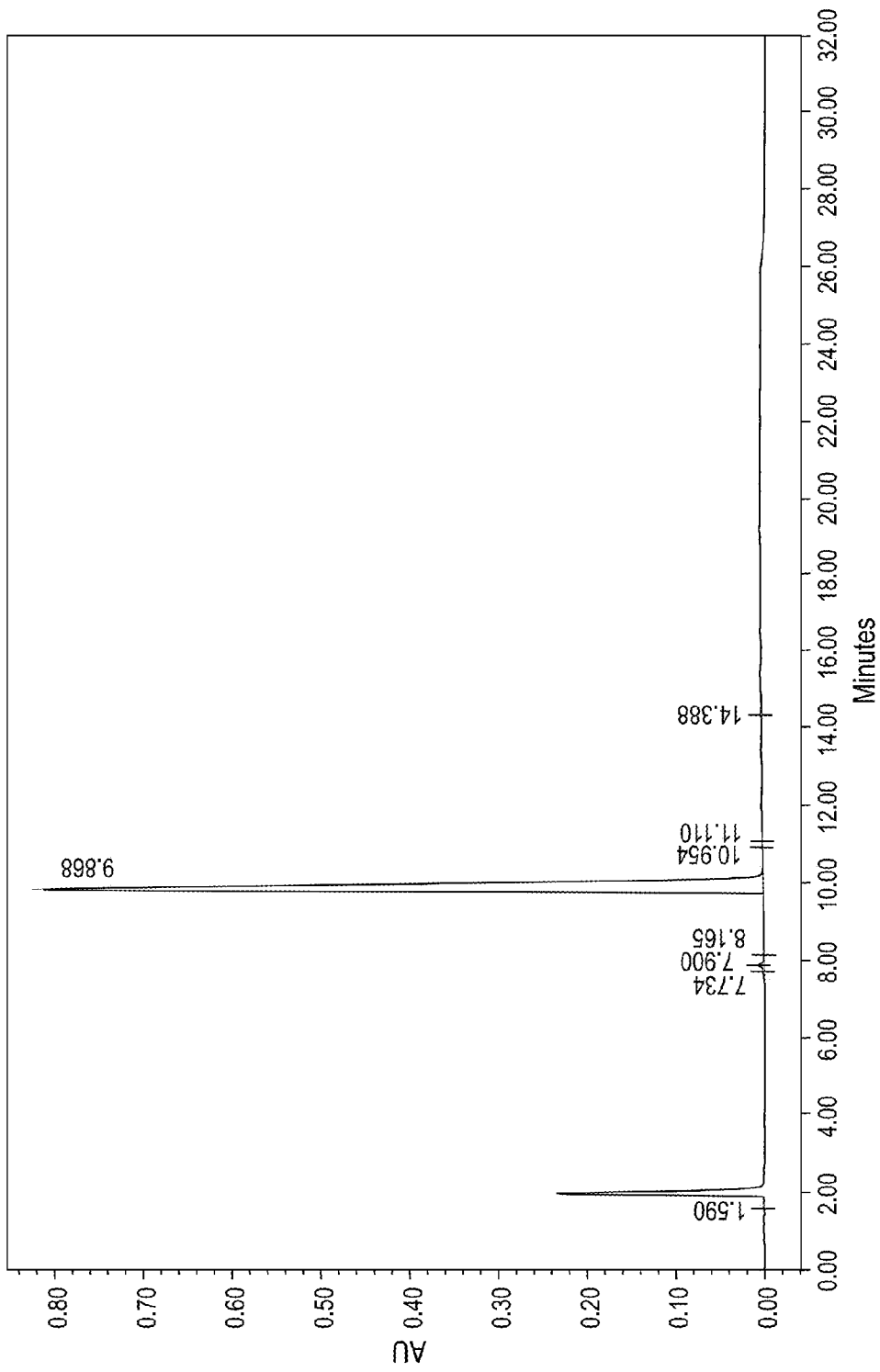
FIG. 17 depicts the HPLC chromatogram of Formula (II) of Example 4 obtained using the HPLC method 1 of FIG. 18
Figure 19:
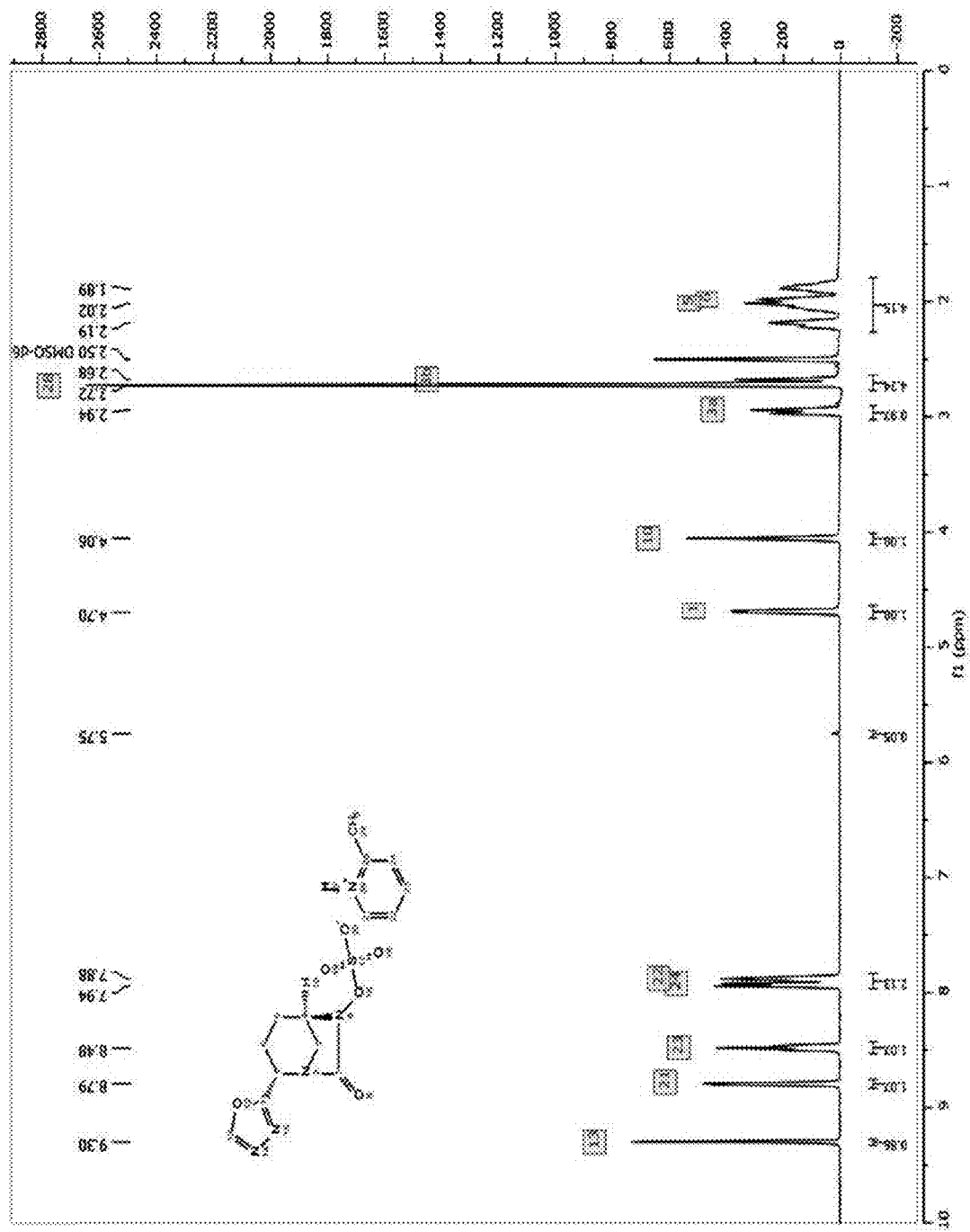
FIG. 19 depicts the $^1$H-NMR spectrum of Formula (II) of Example 9.
Figure 20:
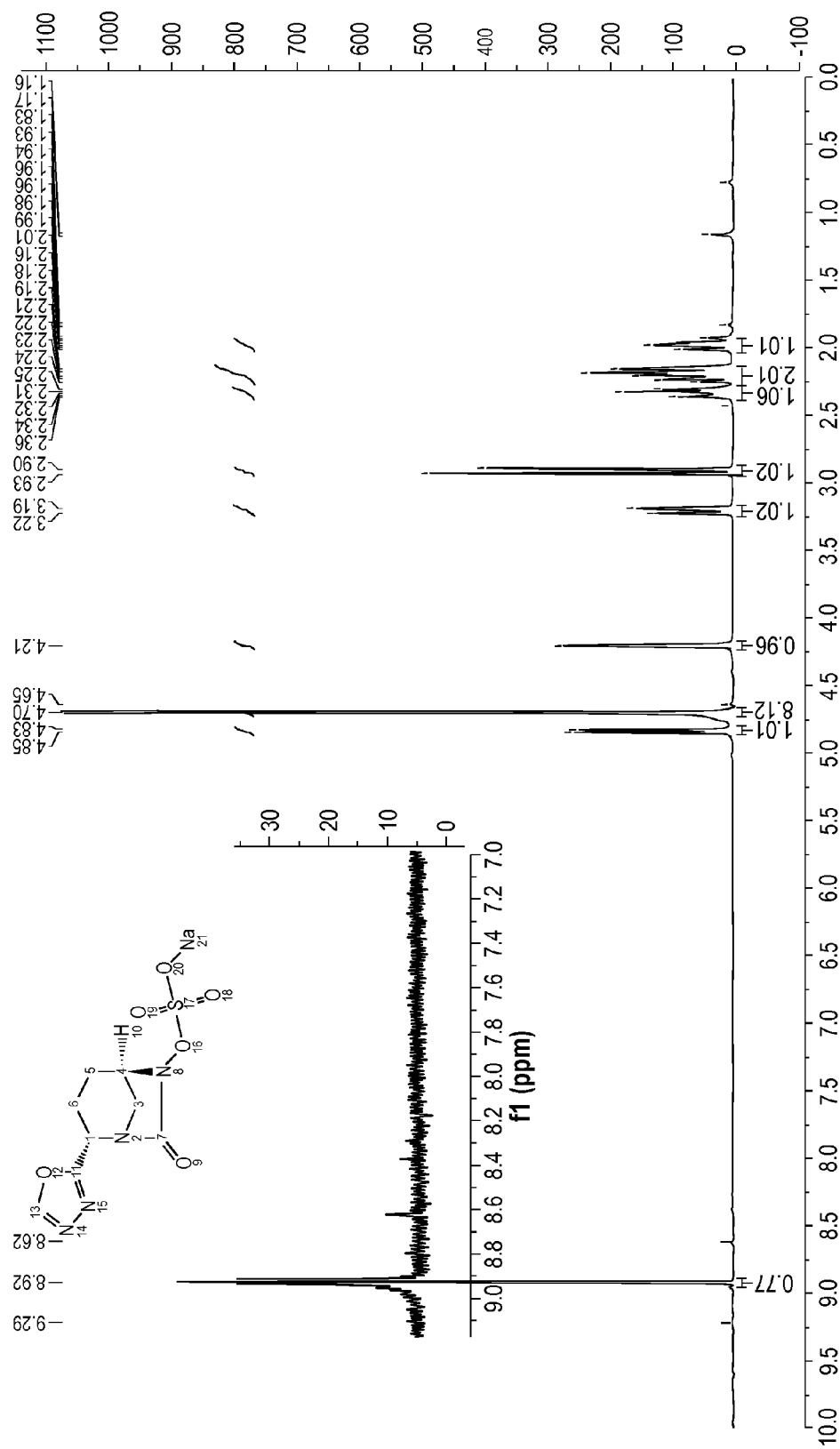
FIG. 20 depicts the $^1$H-NMR spectrum of Formula (III) of Example 9.

The product was analyzed by NMR and HPLC (FIGS. 15-17).

Example 5

Preparation of 2-methylpyridin-1-ium (2S,5R)-2-(1,3,4-oxadiazol-2-yl)-7-oxo-1,6-diazabicyclo[3.2.1]octan-6-yl sulfate by a Non-Crystalizing Process Step 1. Preparation of 2-Picoline/Sulfur Trioxide Complex (Reagent Formation)

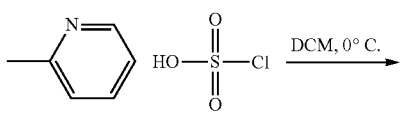

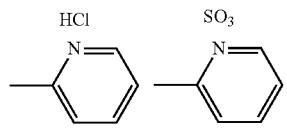

To a 50 ml 3-neck RBF equipped with a magnetic stir bar, thermocouple probe, addition funnel, nitrogen inlet adapter, and a rubber septum, was charged anhydrous dichloromethane (Volume: 7.5 ml) and 2-picoline (4.38 ml, 44.2 mmol). The mixture was chilled in an ice/NaCl bath to −6.2° C. A solution of chlorosulfonic acid (1.434 ml, 21.41 mmol) in anhydrous dichloromethane (Volume: 7.5 ml) was added over 30 minutes, with the temperature being maintained below 5° C., to give an orange solution. The solution was stirred for 30 minutes, split solution into 2 equal parts (9.5 ml each). One part was added to the sulfation reaction at room temperature as described in this Example, step 2.

Step 2. Preparation of 2-methylpyridin-1-ium (2S, 5R)-2-(1,3,4-oxadiazol-2-yl)-7-oxo-1,6-diazabicyclo[3.2.1]octan-6-yl sulfate (Sulfation)

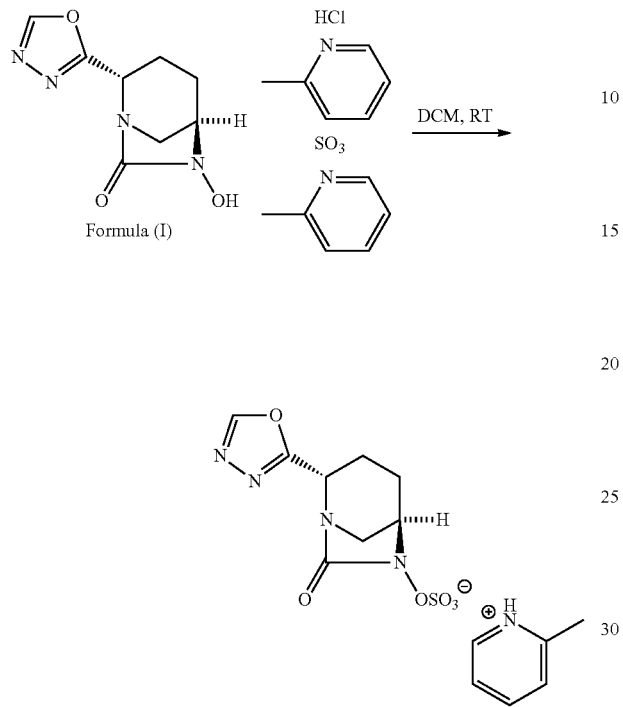

To a 25 mL RBF equipped with a nitrogen needle, rubber septum and a magnetic stir bar containing (2S,5R)-6-hydroxy-2-(1,3,4-oxadiazol-2-yl)-1,6-diazabicyclo[3.2.1]octan-7-one, (Formula (I)) (1.5 g, 7.14 mmol) was charged 10 vol THF (Volume: 15 ml) and stirred at room temperature. Half of the 2-picoline/SO$_3$ complex in 5 vol of DCM prepared according to this Example, step 1, was added. The reaction mixture was stirred at room temperature. Within several minutes, solid dissolved but the mixture became bi-phasic. After ~45 minutes, some solids were present, but about half were caked to the walls of the flask.

After 18 hours, HPLC analysis showed that the reaction was complete, with 98.4% Formula (II) and 0.5% Formula (I).

C. Work-Up

The reaction mixture was cooled in an ice bath for 1 h. The solid in the mixture was filtered off and washed with 5 vol (7.5 ml) of cold THF to give a clumpy, sticky, peach colored solid. The solid was very clumpy and waxy and needed to be broken up, both in the flask and on the filter. After drying overnight, 2-methylpyridin-1-ium (2S,5R)-2-(1,3,4-oxadiazol-2-yl)-7-oxo-1,6-diazabicyclo[3.2.1]octan-6-yl sulfate (Formula (II)) (3.62 g, 9.44 mmol, 132% yield) was obtained as a sticky, waxy yellowish-orange solid.

HPLC showed that the solid was only 87.5% pure, which is a significant decrease as compared to 98.4% in the reaction mixture, with 0.79% starting material (Formula (I)) as compared to 0.5% in the reaction mixture. $^1$H NMR showed a 1.5 eq excess of 2-picoline.

Example 6

Synthesis of 5-ethyl-2-methylpyridin-1-ium (2S,5R)-2-(1,3,4-oxadiazol-2-yl)-7-oxo-1,6-diazabicyclo[3.2.1]octan-6-yl sulfate (Compound 3)

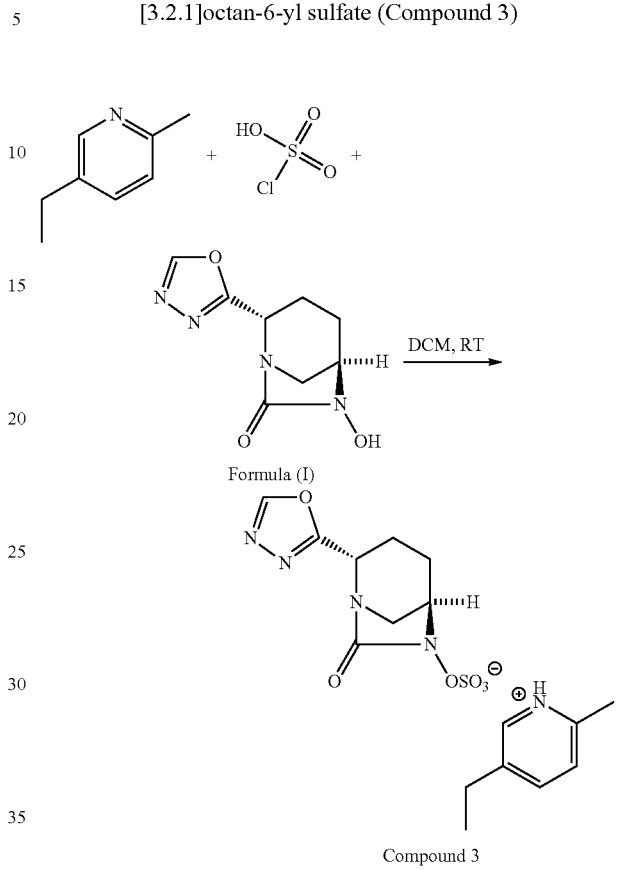

Compound 3

Step 1. Reagent Formation

To a separate 25 ml 3-neck RBF equipped with a magnetic stir bar, thermocouple probe, addition funnel, nitrogen inlet, and a rubber septum, was charged with dichloromethane (5.00 ml) and 5-ethyl-2-methylpyridine (3.45 ml, 26.2 mmol). This mixture was chilled in an ice/NaCl bath to −0.8° C. (target 0 to −5° C.). Then a solution of chlorosulfonic acid (0.828 ml, 12.37 mmol) in dichloromethane (5.00 ml) was added slowly, with the temp being maintained below 5° C. (addn time=40 min), to give a pale yellow solution. After being stirred for 30 minutes, this mixture was added to the Formula (I) mixture in DCM, as described in this Example, step 2.

Step 2. Sulfation

To a 50 mL 3-neck RBF equipped with a nitrogen needle, rubber septum and a magnetic stir bar containing (2S,5R)-6-hydroxy-2-(1,3,4-oxadiazol-2-yl)-1,6-diazabicyclo[3.2.1]octan-7-one (Formula (I)) (2.00 g, 9.52 mmol) was charged with dichloromethane (10.00 ml) and stirred at room temperature. The 5-ethyl-2-methylpyridine/sulfur trioxide complex in dichloromethane prepared according to this Example, step 1, was added.

Upon addition of 5-ethyl-2-methylpyridine/sulfur trioxide complex, Formula (I) dissolved within the first 15 minutes and reaction mixture remained clear and pale-yellow colored. After 17 hours, the reaction mixture contained 4.9% Formula (I), and 85.14% Compound 3.

C. Work-Up:

The reaction mixture was cooled in an ice bath. No crystallization was observed. After addition of up to 20 ml THF the reaction mixture, there was still no crystallization. The reaction mixture was then concentrated to a thick oil on rotovap with a bath temperature of 20° C. 20 ml THF was added to the oil, but no crystallization was observed. After reconcentration on rotovap, Compound 3 was obtained as a yellow sticky semisolid (6.10 g, 14.83 mmol, 156% yield).

Example 7

Synthesis of 2,6-dimethylpyridin-1-ium (2S,5R)-2-(1,3,4-oxadiazol-2-yl)-7-oxo-1,6-diazabicyclo[3.2.1]octan-6-yl sulfate (Compound 4)

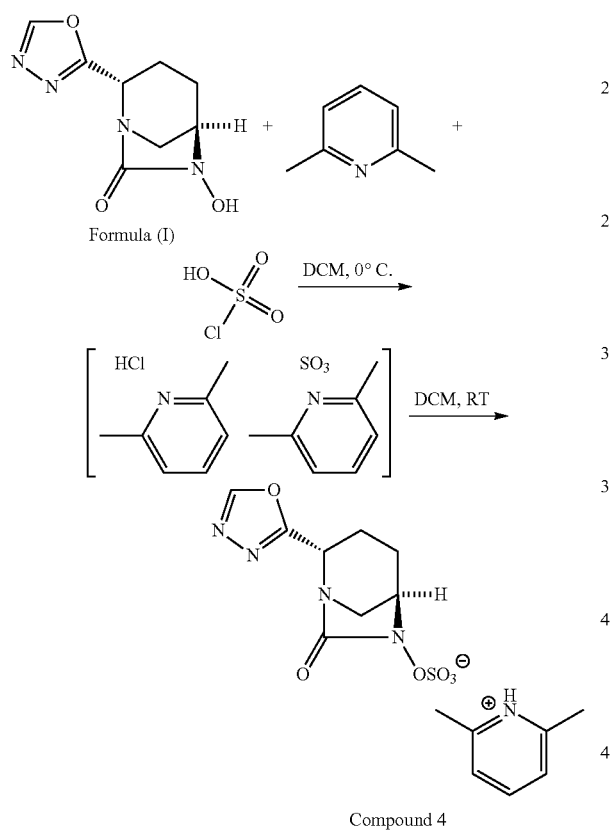

Step 1. Reagent Formation

To a 25 ml 3-neck RBF equipped with a magnetic stir bar, thermocouple probe, addition funnel, nitrogen inlet adapter, and a rubber septum was charged dichloromethane (anh) (5.00 ml) and 2,6-Lutidine (3.05 ml, 26.2 mmol). The lutidine solution was chilled in an ice/NaCl bath to −2.0° C. (target 0 to −5° C.). Then a solution of chlorosulfonic acid (0.828 ml, 12.37 mmol) in dichloromethane (anh) (5.00 ml) was added slowly, with temp being maintained below 5° C. (addition time=30 min), to give a thin slurry, orange to pink in color. The reaction mixture was stirred for 1 h. The solid formed in the solution was filtered off.

Step 2. Sulfation

To a 25 mL RBF with a nitrogen needle, rubber septum and a magnetic stir bar containing (2S,5R)-6-hydroxy-2-(1,3,4-oxadiazol-2-yl)-1,6-diazabicyclo[3.2.1]octan-7-one (Formula (I)) (2.00 g, 9.52 mmol) was charged dichloromethane (anh) (10.00 ml) and stirred at RT. The filtrate obtained in the step of reagent formation (above) was added. The reaction mixture was stirred at RT and began to get clear almost immediately. After 15 hours, Reaction A is complete, with 0.04% Formula (I) and 98.83% Compound 4.

C. Work-Up:

The reaction mixture was cooled in an ice/water/NaCl bath to 0° C. and filtered to remove 200 mg of a solid containing no desired product. The resulting filtrate was concentrated on a rotovap and dried under high vac overnight, providing Compound 4 (Yield: 5.71 g). NMR analysis showed that the product contained a 1.3 eq excess of lutidine.

Example 8

Synthesis of Sodium(2S,5R)-2-(1,3,4-oxadiazol-2-yl)-7-oxo-1,6-diazabicyclo[3.2.1]octan-6-yl sulfate (Formula (III)) (Conversion of 2-methylpyridin-1-ium (2S,5R)-2-(1,3,4-oxadiazol-2-yl)-7-oxo-1,6-diazabicyclo[3.2.1]octan-6-yl sulfate (Formula (II)) to sodium (2S,5R)-2-(1,3,4-oxadiazol-2-yl)-7-oxo-1,6-diazabicyclo[3.2.1]octan-6-yl sulfate (Formula (III)))

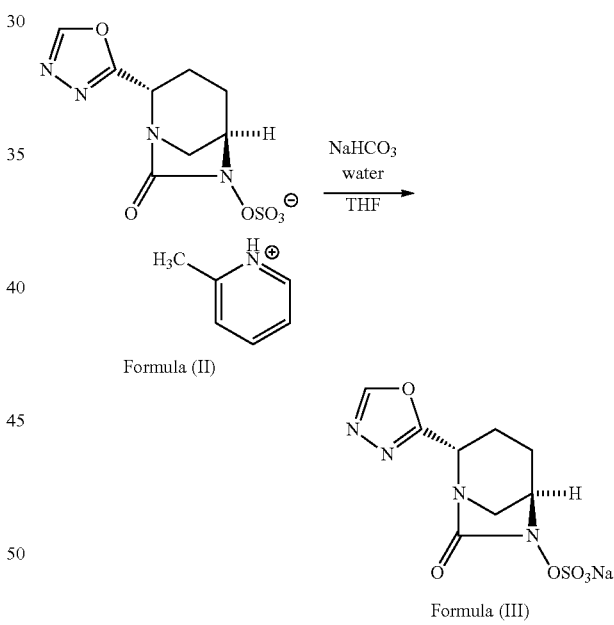

Formula (II) (11.4 g, 30 mmol) was suspended in water (18.1 mL). NaHCO$_3$ (2.56 mg, 30.3 mmol) was added into the suspension (endothermic reaction to ~13° C.). CO$_2$ gas evolution was observed. The reaction mixture was stirred at room temperature for 2 h (clear solution, CO$_2$ evolution ceased). THF (27 mL) was added and the solution was polish filtered through a pad of celite. The celite was rinsed with 1:2 water-THF (1.5 mL). The combined filtrate and washes was diluted with THF (480 mL) over 30 min, with solid formation observed during the addition. The suspension was stirred at RT for 16 h. The solid was collected by filtration, rinsed twice with THF (2×30 mL) and dried at RT under vacuum to afford 9.59 g of Formula (III) (Yield: 87%).

Example 9

Alternative Salt Conversion Procedures

A. A variety of reaction conditions can be used to form sodium (2S,5R)-2-(1,3,4-oxadiazol-2-yl)-7-oxo-1,6-diazabicyclo[3.2.1]octan-6-yl sulfate (Formula (III)) from 2-methylpyridin-1-ium (2S,5R)-2-(1,3,4-oxadiazol-2-yl)-7-oxo-1,6-diazabicyclo[3.2.1]octan-6-yl sulfate (Formula (II)).

| Conditions | Solvent | Temp | Time | Results | |
|---|---|---|---|---|---|
| IPA, Na source: Hexanoic, Octanoic, 2-ethylhexanoic, butyric | IPA | RT | 18 h | Experiments in IPA lead to difficult filtrations, gummy, gel like products, low potent solids, and overall poor results. IPA should not be used as solvent for salt exchange. | |
| THF, Na source: acetic, Hexanoic, Octanoic, 2-ethylhexanoic, butyric, propionic, pivalic, hexanoic | THF (50 V) | RT | 18 h | Sample<br>Na acetate<br>Na propionate<br>Na butyrate<br>Na pivalate<br>Na hexanoate<br>Na 2-ethylhexanoate<br>Na octanoate | Yield<br>71.00%<br>89.00%<br>71.40%<br>92.60%<br>99.50%<br>93.30%<br>90.60% |
| Solvent Screen with Na 2-Ethylhexanoate | THF/H2O | RT | 18 h | 84.4% yield | 98.86% purity (HPLC 1) |
| | THF | RT | 18 h | 88.8% yield | 98.95% purity (HPLC 1) |
| | MEK/H2O | RT | 18 h | 81.4% yield | 98.28% purity (HPLC 1) |
| | IPAC/H2O | RT | 18 h | 96.0% yield | 99.05% purity (HPLC 1) |
| | EtOAc/H2O | RT | 18 h | 82.6% yield | 98.8% purity (HPLC 1) |

|  | Weight (g) | Weight % | KF | |
|---|---|---|---|---|
| Water | 15.47 | 1.65% | | |
| Isopropyl Acetate | 861.8 | 91.64% | 1-1.75% | 2-1.75% |
| Na 2-ethylhexanoate | 63.12 | 6.71% | 1.74% | |
| Total | 940.39 | | | |

B. A representative procedure for the conversion of Formula (II) to Formula (III):

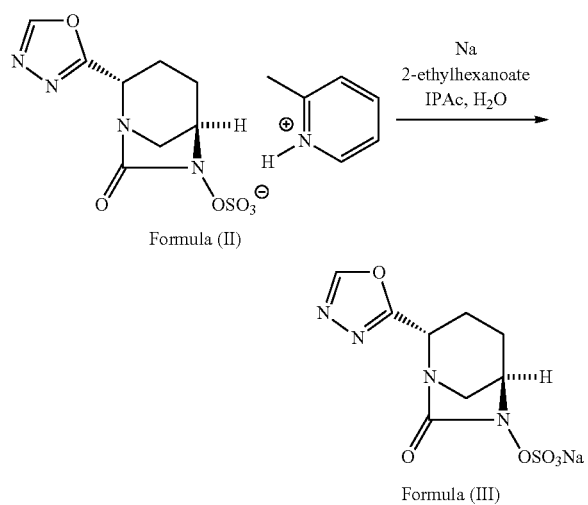

Formula (II)

Formula (III)

A stock solution of water (1.5-1.8% w/w target) and sodium 2-ethylhexanoate (6.5-7% w/w target) in isopropyl acetate (IPAc) was prepared according to the following procedure: To a 1000 mL reactor equipped with thermocouple, stirrer, N₂ inlet, and baffle, with a T$_j$ set to 25° C. was charged the following in order:

The water was charged first, then IPAc. This mixture was stirred 20 min to ensure homogeneity and then two samples for KF (Karl Fischer) titration were taken. To this was added the Na 2-ethylhexanoate in one portion and stirred 10 min, though homogeneity was obtained quickly. The stock was stored at 22° C. for later use.

Salt Conversion:

The experiment was performed in a 1000 mL reactor equipped with stirrer (anchor), thermocouple, baffle, and N₂ inlet, with a jacket temp (T$_j$) set to 25° C. To the reactor was charged the 2-methylpyridin-1-ium (2S,5R)-2-(1,3,4-oxadiazol-2-yl)-7-oxo-1,6-diazabicyclo[3.2.1]octan-6-yl sulfate (58.286 g, 152 mmol). The lid was attached and an addition funnel with the stock prepared above was setup. To the reactor was added the stock made up of Isopropyl acetate (Calculated Volume: 645 ml, Volume Ratio: 11.07, Ratio: 1.000), 1.74% w/w water (645 ml, 526 mmol), and 6.71% w/w Sodium 2-ethylhexanoate (645 ml, 232 mmol). Then stirring was initiated at 520 rpm. Stirring was increased to 800 rpm before solids were dislodged from bottom of reactor. Significant splatter and crusting was observed. The stirring was stopped and the particles settled quickly (<5 min). The reactor lid was opened and 20 mL of wet IPAc was used to wash down the crusts. The lid was replaced and the stirring reinitiated at 160 rpm, enough to maintain the particles suspended in solution and a slurry that appeared to contain evenly distributed particles.

After stirring 6 h, the suspension was drained from the reactor to a 1000 mL bottle and filtered through a Whatman 541 filter paper (11 cm) in a Buchner funnel under vacuum. The bottle was rinsed with Isopropyl acetate (Calculated Volume: 150 ml, Volume Ratio: 2.57, Ratio: 1.000) to transfer the remaining solids. The 1000 mL reactor did not appear to have significant solids remaining so no reactor wash was performed. The cake was then washed with Isopropyl acetate (Calculated Volume: 700 ml, Volume Ratio: 12.01, Ratio: 1.000) and dried under vacuum 35 min.

The solids were discharged, weighed, and analyzed by HPLC 1 (FIG. 18). The final powder sodium (2S,5R)-2-(1,3,4-oxadiazol-2-yl)-7-oxo-1,6-diazabicyclo[3.2.1]octan-6-yl sulfate (53.245 g, 171 mmol, 112% yield, 98% potency corrected) was stored at −20° C.

TABLE 1

Summary data for representative sodium salt conversion

| Sample | wt. (g) | Potency (ug/mg) | Corr. wt (g) | Mol. | % yield (corr.) | HPLC 1 Purity (%) | Picoline content (NMR) |
|---|---|---|---|---|---|---|---|
| Starting picoline salt | 58.286 | 730 | 42.549 | 147.10 mmol | — | 86.25 98.98% w/o pic | 1 molar eq. |
| Product sodium salt | 53.245 | 790 | 42.064 | 145.43 mmol | 98.8% | 99.10% | n.d. |

Example 10

Figure 21A:
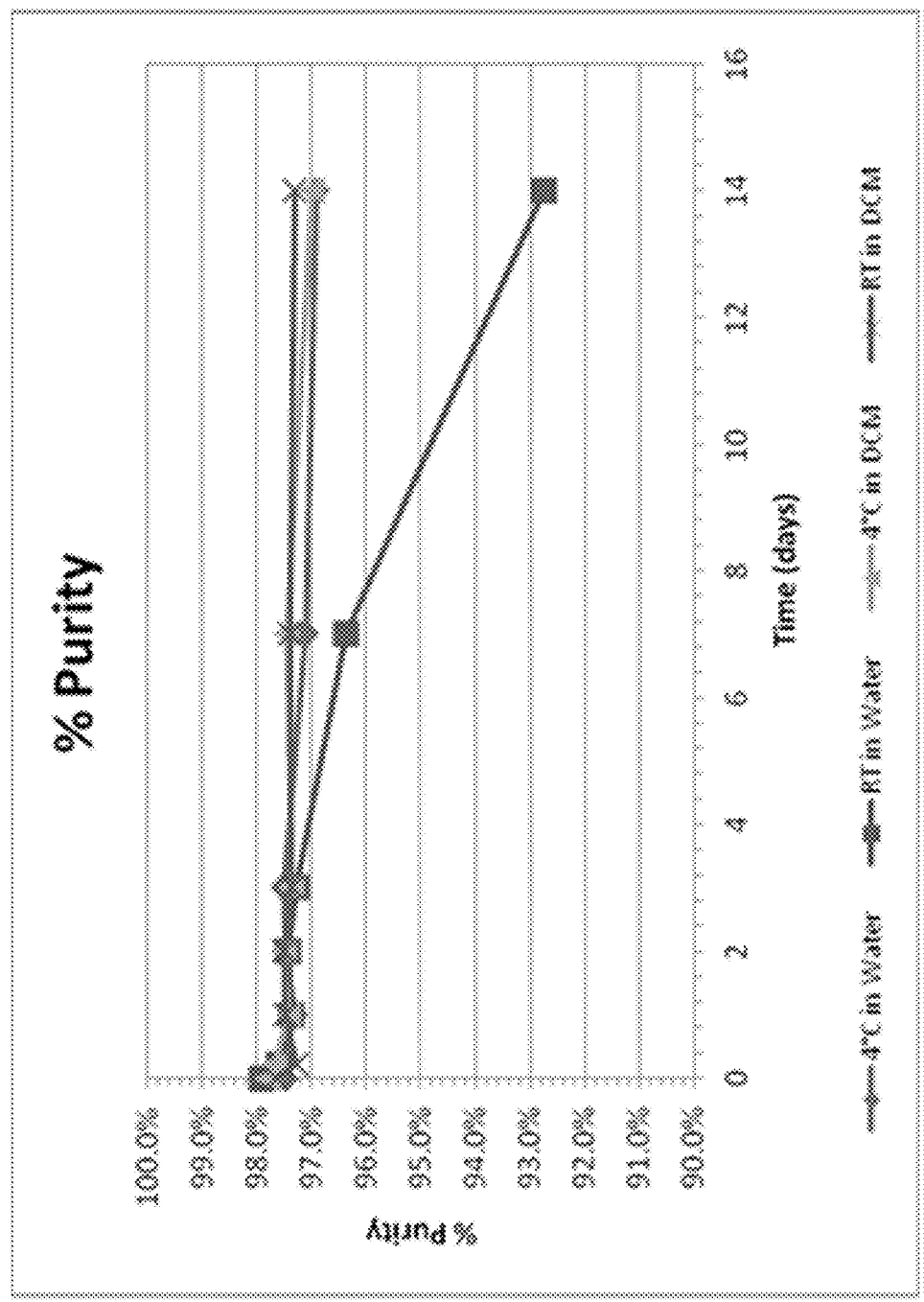
FIG. 21A depicts the purity change relative to starting purity of TBA salt in water and DCM at 4° C. and room temperature (see Example 10).

As part of the program to improve the process for the manufacture of the sodium salt of (2S,5R)-2-(1,3,4-oxadiazol-2-yl)-7-oxo-1,6-diazabicyclo[3.2.1]octan-6-yl hydrogen sulfate, a new intermediate capable of isolation and utility in the production was sought. In early clinical productions, the picoline salt of (2S,5R)-2-(1,3,4-oxadiazol-2-yl)-7-oxo-1,6-diazabicyclo[3.2.1]octan-6-yl hydrogen sulfate was found to be unstable in solution and was converted to the tetrabutylammonium (TBA) salt, an organic soluble form of (2S,5R)-2-(1,3,4-oxadiazol-2-yl)-7-oxo-1,6-diazabicyclo[3.2.1]octan-6-yl hydrogen sulfate. It was found that in order to convert the TBA form of the product to the desired sodium (Na) form, a resin exchange step was required (see, e.g., Example 12). This was performed in aqueous solution and high dilution (~1 wt %) and therefore solution stability of the TBA salt in aqueous environments was examined and found to be a risk for long term scale-up (see FIGS. 21A and 21B).

Figure 22A:
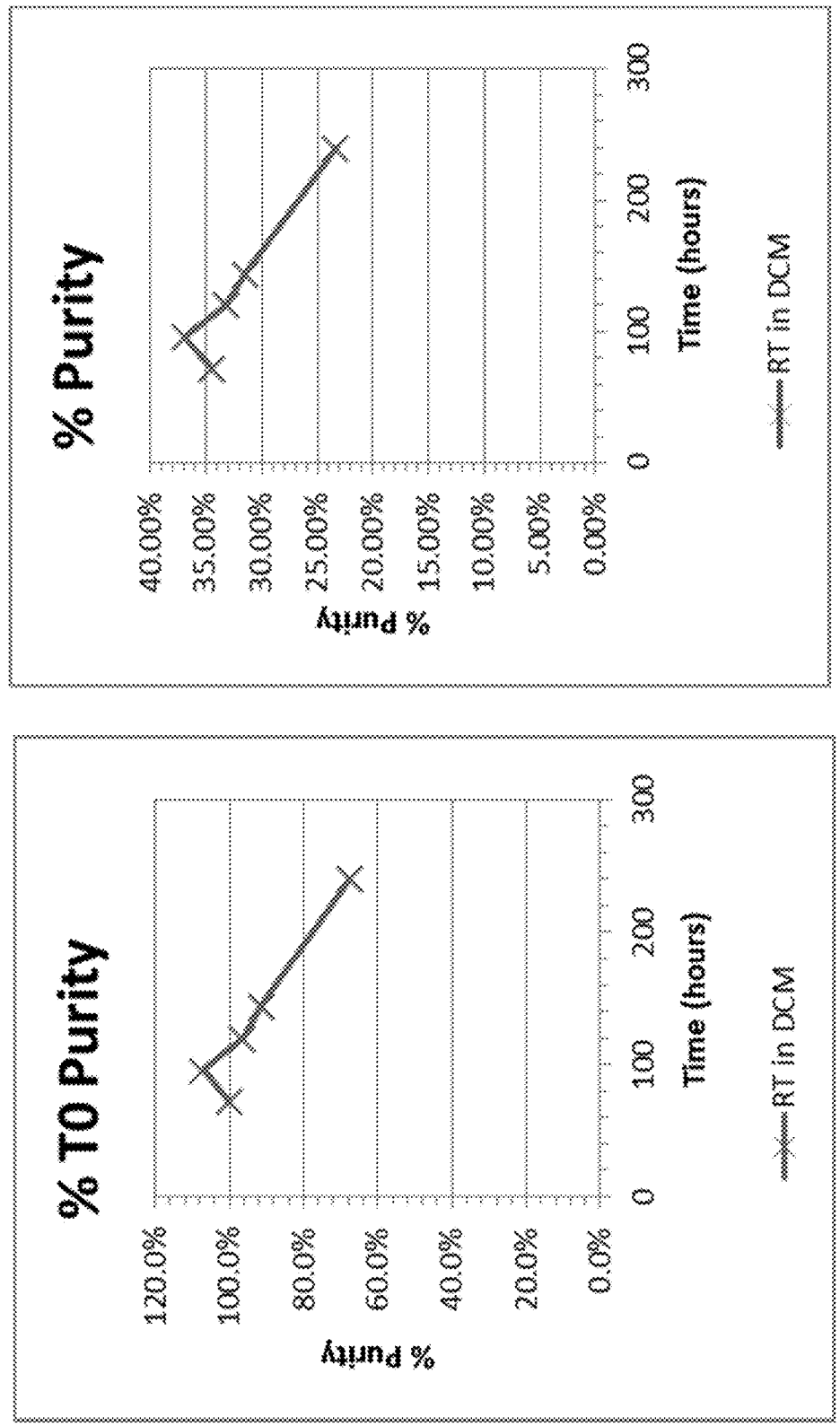
FIG. 22A depicts the purity change relative to starting purity of the picoline salt (Formula (II)) in DCM at room temperature (RT) (see Example 10).

Additionally, the picoline salt precursor was examined for solution stability as an alternative hold point for the process. In short, the solution stability of the picoline salt in dichloromethane solution was significantly inferior to the TBA salt (see FIGS. 22A and 22B).

Thus, the stability of the different salt precursors of the (2S,5R)-2-(1,3,4-oxadiazol-2-yl)-7-oxo-1,6-diazabicyclo[3.2.1]octan-6-yl hydrogen sulfate API were a major factor for consideration in scale-up. Also, the volume inefficiency, throughput bottlenecks, and impurity generation associated with the TBA to Na salt resin exchange process created the need for an improved step. Accordingly, there was a need for a stable solid that could be isolated, stored, and be used as needed to produce the desired sodium API in a reliable, scalable process. In screening different salt forms and examining the potential for crystallizations (as a means to isolate the salt forms), the TBA, pyridine, 5-ethyl-2-methylpyridine, and 2,6-lutidine forms of the API were not able to be successfully isolated in solid form. However, unexpectedly, the 2-picoline salt form of the API was found to be stable (see, e.g., FIG. 23) and useful in the production of the sodium salt form of the API as demonstrated herein.

Example 11

Synthesis of the Compound of Formula (I)

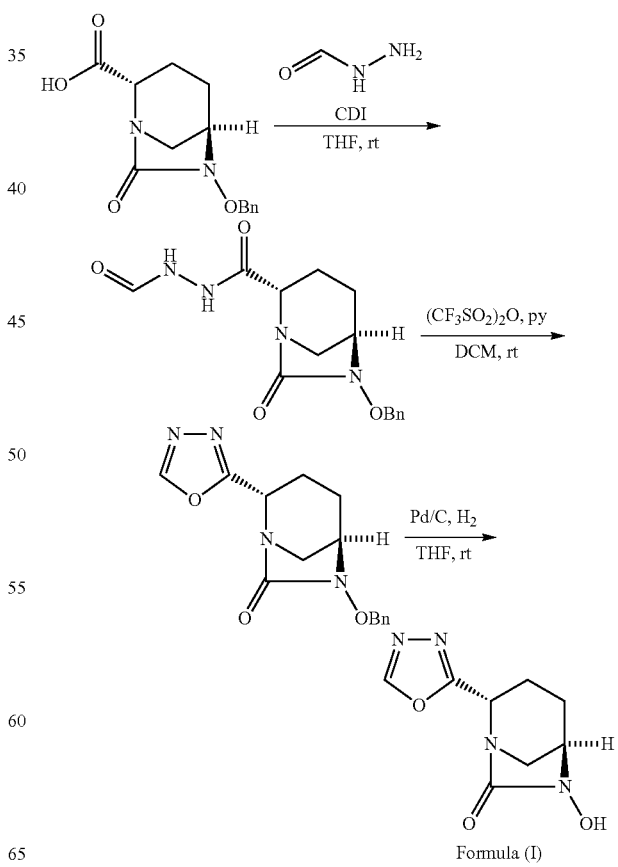

Formula (I)

Step 1: 1,1'-Carbonyldiimidazole (5.8 g, 36.2 mmol) was added to a 0° C. solution of (2S,5R)-6-(benzyloxy)-7-oxo-1,6-diazabicyclo[3.2.1]octane-2-carboxylic acid (5.0 g, 18.1 mmol) in dry THF (200 mL). The reaction mixture was allowed to warm to rt then was stirred at rt for 3 hrs. Formohydrazide (5.4 g, 90.5 mmol) was added in one portion, and the reaction mixture was stirred for additional 3 hrs. The mixture was then diluted with saturated sodium chloride and extracted with EtOAc (3×). The combined organic layer was washed with saturated sodium chloride (2×), dried over Na$_2$SO$_4$, and concentrated to afford crude (2S,5R)-6-(benzyloxy)-N'-formyl-7-oxo-1,6-diazabicyclo[3.2.1]octane-2-carbohydrazide (~11 g), which was directly used in the next step. ESI-MS (EI$^+$, m/z): 319.1 [M+H]$^+$.

Step 2: To a −10° C. solution of (2S,5R)-6-(benzyloxy)-N'-formyl-7-oxo-1,6-diazabicyclo[3.2.1]octane-2-carbohydrazide (11 g) in dry DCM (200 mL) was added pyridine (28 mL), followed by dropwise addition of (CF$_3$SO$_2$)$_2$O (28 mL). The reaction mixture was allowed to warm to rt and was stirred for 3 hrs. The reaction mixture was then cooled to −10° C. and quenched with sat. NaHCO$_3$. The organic layer was separated and the aqueous layer was extracted with EtOAc (3×). The combined organic layer was dried over Na$_2$SO$_4$, concentrated and purified by silica gel column chromatography (gradient elution 1:3 to 2:1 EtOAc/hexanes) to give (2S,5R)-6-(benzyloxy)-2-(1,3,4-oxadiazol-2-yl)-1,6-diazabicyclo[3.2.1]octan-7-one (4.6 g, 86% for two steps) as a slightly yellow solid. ESI-MS (EI$^+$, m/z): 301.0 [M+H]$^+$.

Step 3: To a solution of (2S,5R)-6-(benzyloxy)-2-(1,3,4-oxadiazol-2-yl)-1,6-diazabicyclo[3.2.1]octan-7-one (4.6 g, 15.3 mmol) in THF (150 mL) was added 10% Pd/C (1 g). The mixture was stirred under H$_2$ atmosphere at rt for 3 hrs. The reaction mixture was then filtered and concentrated to afford the compound of Formula (I): (2S,5R)-6-hydroxy-2-(1,3,4-oxadiazol-2-yl)-1,6-diazabicyclo[3.2.1]octan-7-one (2.9 g, 91%). ESI-MS (EI$^+$, m/z): 211.1 [M+H]$^+$.

Example 12

Comparative Synthesis of a Compound of Formula (III) (Sodium (2S,5R)-2-(1,3,4-oxadiazol-2-yl)-7-oxo-1,6-diazabicyclo[3.2.1]octan-6-yl sulfate)

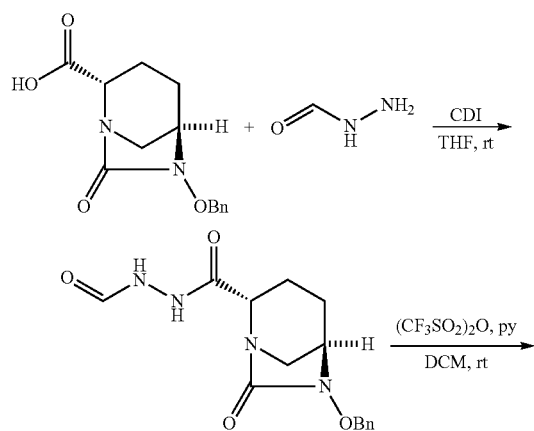

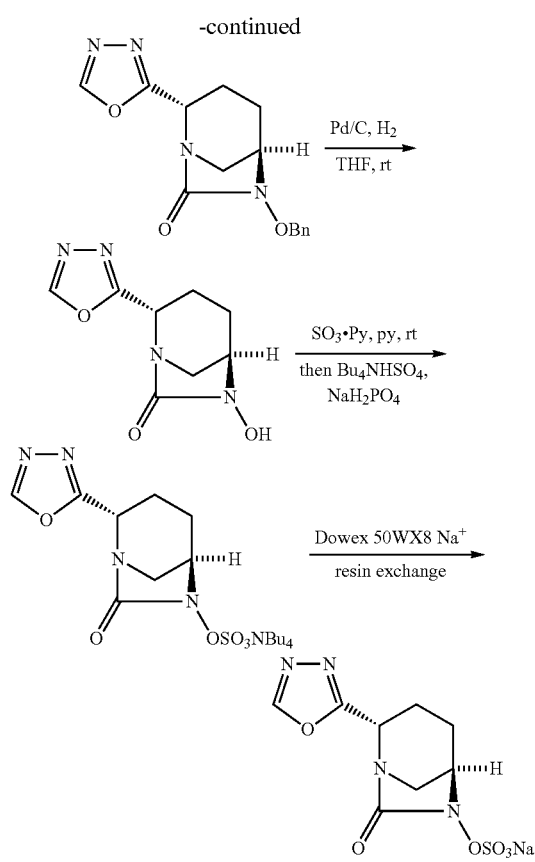

The following procedure is described in U.S. Publication No. US 2013/0296290, which is hereby incorporated by reference in its entirety Step 1: See step 1 of Example 11.
Step 2: See step 2 of Example 11.
Step 3: See step 3 of Example 11.
Step 4: To a solution of (2S,5R)-6-hydroxy-2-(1,3,4-oxadiazol-2-yl)-1,6-diazabicyclo[3.2.1]octan-7-one, Formula (I) (2.9 g, 13.8 mmol) in dry pyridine (60 mL) was added SO$_3$.Py (11.0 g, 69.0 mmol). The reaction mixture was stirred at rt for 8 hrs and then concentrated under vacuum. The residue was re-dissolved in aqueous NaH$_2$PO$_4$ (1.5 M, 100 mL) then tetrabutylammonium hydrogensulphate (5.88 g, 17.3 mmol) was added. The mixture was stirred at rt for 20 minutes, then was extracted with EtOAc (4×). The combined organic layer was dried and concentrated and the residue was purified by silica gel column chromatography (gradient elution 10:1 to 2:1 DCM/acetone) to afford tetrabutylammonium (2S,5R)-2-(1,3,4-oxadiazol-2-yl)-7-oxo-1,6-diazabicyclo[3.2.1]octan-6-yl sulfate (4.1 g, 97%) as a white solid. ESI-MS (EI$^-$, m/z): 289.0 [M−H]$^-$. $^1$H NMR (400 MHz, CDCl$_3$): δ 8.48 (s, 1H), 4.75 (d, J=6.5 Hz, 1H), 4.40 (br s, 1H), 3.34-3.26 (m, 9H), 2.82 (d, J=12.0 Hz, 1H), 2.37-2.25 (m, 3H), 2.06-1.98 (m, 1H), 1.71-1.65 (m, 8H), 1.49-1.42 (m, 8H), 1.01 (t, J=7.5 Hz, 12H).

Step 5: Resin Exchange: Tetrabutylammonium (2S,5R)-2-(1,3,4-oxadiazol-2-yl)-7-oxo-1,6-diaza-bicyclo[3.2.1]octan-6-yl sulfate (4.1 g, 7.72 mmol) was dissolved in a minimum amount of HPLC grade water (~40 mL) and passed through a column of 80 g of DOWEX 50WX 8 Na$^+$ resin (the resin was prewased with >4 L of HPLC grade water) and eluted with HPLC grade water to afford sodium (2S,5R)-2-(1,3,4-oxadiazol-2-yl)-7-oxo-1,6-diazabicyclo[3.2.1]octan-6-yl sulfate (2.2 g, 91%) as a white solid after lyophilization. ESI-MS (EI+, m/z): 291.2 [M+H]+. 1H NMR (300 MHz, D2O) δ 8.92 (s, 1H), 4.84 (d, J=6.7 Hz, 1H), 4.20 (br s, 1H), 3.25-3.16 (m, 1H), 2.92 (d, J=12.3 Hz, 1H), 2.41-2.26 (m, 1H), 2.26-2.11 (m, 2H), 2.04-1.89 (m, 1H).

The invention claimed is:

1. A compound of Formula (II):

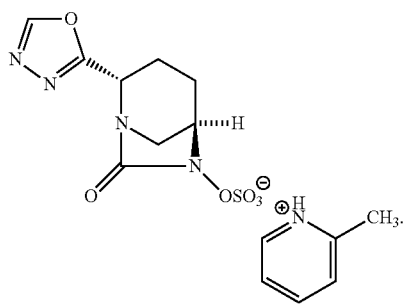

Formula (II)

2. The compound of claim 1 in crystalline form.

3. The compound of claim 2, characterized by an X-ray powder diffraction pattern substantially in accordance with pattern A, B, or C of FIG. 1A.

4. The compound of claim 2, characterized by an X-ray powder diffraction pattern comprising characteristic peaks expressed in degrees 2θ (±0.2) at 10.48, 16.75, 18.27, 20.40, and 28.80.

5. The compound of claim 2, characterized by an X-ray powder diffraction pattern comprising characteristic peaks expressed in degrees 2θ (±0.2) at 10.48, 11.69, 12.00, 12.81, 14.28, 15.69, 16.75, 17.50, 17.70, 18.27, 19.58, 20.40, 21.24, 21.85, 22.48, 23.55, 24.02, 24.26, 25.39, 26.8, 27.33, 28.80, 31.21, 31.67, 32.19, 32.63, 33.89, 35.73, 35.96, 36.30, and 37.82.

6. The compound of claim 2, characterized by an X-ray powder diffraction pattern comprising characteristic peaks express in degrees 2θ (±0.2) at 10.48, 11.69, 12.00, 12.81, 14.28, 15.19, 15.69, 16.19, 16.75, 17.50, 17.70, 18.27, 19.58, 20.40, 20.79, 21.24, 21.85, 22.48, 23.55, 24.02, 24.26, 25.39, 25.66, 26.69, 26.82, 27.33, 28.19, 28.80, 29.16, 29.38, 29.82, 30.46, 31.21, 31.67, 32.19, 32.63, 33.40, 33.89, 34.25, 35.39, 35.73, 35.96, 36.30, 37.82, 38.72, and 38.83.

7. The compound of claim 2, characterized by a differential scanning calorimetry thermogram having an endotherm peak at 139.94° C.±10° C.

8. The compound of claim 2 characterized by a differential scanning calorimetry thermogram having an exotherm peak at 181.77° C.±10° C.

9. The compound of claim 2, characterized by a thermogravimetry curve having an onset temperature of 176.07±10° C.

10. The compound of claim 2, further characterized by a thermo gravimetric analysis indicating a weight loss of 0-6% upon heating from 30±10° C. to 150±10° C.

11. A method for preparing the compound of Formula (II):

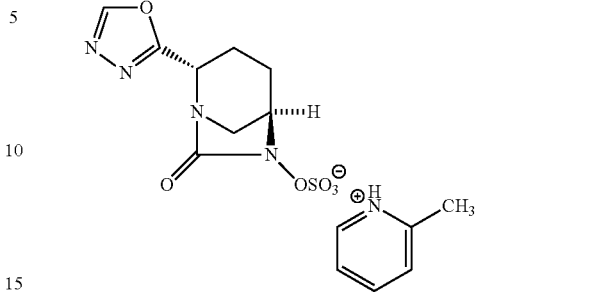

Formula (II)

the method comprising the step of reacting a compound of Formula (I)

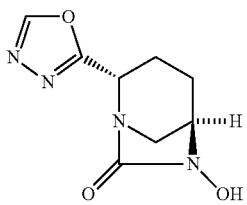

Formula (I)

with a 2-picoline/sulfur trioxide complex in a solvent to form the compound of Formula (II).

12. The method of claim 11, wherein the solvent comprises dichloromethane.

13. The method of claim 11, further comprising the step of isolating the compound of Formula (II).

14. The method of claim 13, wherein the step of isolating the compound of Formula (II) comprises crystalizing the compound of Formula (II).

15. The method of claim 11, wherein the compound of Formula (II) is crystalline.

16. A crystalline piccoline salt of a compound of Formula (I)

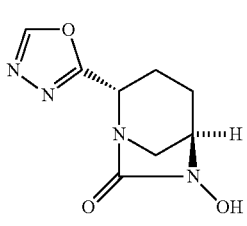

Formula (I)

characterized by an X-ray powder diffraction pattern comprising characteristic peaks expressed in degrees 2θ (±0.2) at 10.5, 16.8, 18.3, 20.4, and 28.8.

17. The compound of claim 16, characterized by an X-ray powder diffraction pattern comprising characteristic peaks expressed in degrees 2θ (±0.2) at 10.48, 11.69, 12.00, 12.81, 14.28, 15.69, 16.75, 17.50, 17.70, 18.27, 19.58, 20.40, 21.24, 21.85, 22.48, 23.55, 24.02, 24.26, 25.39, 26.8, 27.33, 28.80, 31.21, 31.67, 32.19, 32.63, 33.89, 35.73, 35.96, 36.30, and 37.82.

18. The compound of claim 16, characterized by a differential scanning calorimetry thermogram having an endotherm peak at 139.94° C.±10° C.

19. The compound of claim 16, characterized by a differential scanning calorimetry thermogram having an exotherm peak at 181.77° C.±10° C.

20. The compound of claim 16, characterized by a thermogravimetry curve having an onset temperature of 176.07±10° C.

21. The compound of claim 16, further characterized by a thermo gravimetric analysis indicating a weight loss of 0-6% upon heating from 30±10° C. to 150±10° C.

22. The compound of claim 16, obtained by a process comprising the step of reacting a compound of Formula (I)

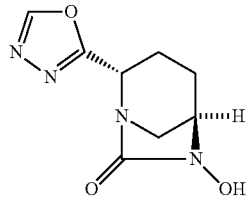

Formula (I)

with a 2-picoline/sulfur trioxide complex in a solvent to form the compound of Formula (II).

* * * * *